(12) United States Patent
Binder et al.

(10) Patent No.: US 8,680,264 B2
(45) Date of Patent: Mar. 25, 2014

(54) CHEMICAL TRANSFORMATION OF LIGNOCELLULOSIC BIOMASS INTO FUELS AND CHEMICALS

(71) Applicants: Joseph Bartholomew Binder, Berkeley, CA (US); Ronald Thaddeus Raines, Madison, WI (US)

(72) Inventors: Joseph Bartholomew Binder, Berkeley, CA (US); Ronald Thaddeus Raines, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/664,198

(22) Filed: Oct. 30, 2012

(65) Prior Publication Data

US 2013/0158254 A1   Jun. 20, 2013

Related U.S. Application Data

(63) Continuation of application No. 12/485,755, filed on Jun. 16, 2009, now Pat. No. 8,324,376.

(60) Provisional application No. 61/073,285, filed on Jun. 17, 2008.

(51) Int. Cl.
*C07H 1/00*       (2006.01)
*C07H 3/00*       (2006.01)
*C08B 37/00*      (2006.01)

(52) U.S. Cl.
USPC .......................................................... 536/124

(58) Field of Classification Search
None
See application file for complete search history.

(56) References Cited

U.S. PATENT DOCUMENTS

| | | | |
|---|---|---|---|
| 2,223,714 | A | 12/1940 | Bates et al. |
| 2,750,394 | A | 6/1956 | Peniston |
| 2,917,520 | A | 12/1959 | Cope |
| 2,929,823 | A | 3/1960 | Garber et al. |
| 3,007,941 | A | 11/1961 | Copelin et al. |
| 3,118,912 | A | 1/1964 | Smith |
| 3,257,417 | A | 6/1966 | Dunlop et al. |
| 4,154,744 | A | 5/1979 | Hamada et al. |
| 4,278,790 | A | 7/1981 | McCormick |
| 4,339,387 | A | 7/1982 | Fleche et al. |
| 4,740,605 | A | 4/1988 | Rapp |
| 4,764,627 | A | 8/1988 | Diebold et al. |
| 4,780,552 | A | 10/1988 | Wambach et al. |
| 4,897,497 | A | 1/1990 | Fitzpatrick |
| 4,971,657 | A | 11/1990 | Avignon et al. |
| 5,347,018 | A | 9/1994 | Clark, Jr. et al. |
| 5,562,777 | A | 10/1996 | Farone et al. |
| 5,597,714 | A | 1/1997 | Farone et al. |
| 5,726,046 | A | 3/1998 | Farone et al. |
| 6,423,145 | B1 | 7/2002 | Nguyen et al. |
| 6,603,026 | B2 | 8/2003 | Lightner |
| 7,572,925 | B2 | 8/2009 | Dumesic et al. |
| 7,880,049 | B2 | 2/2011 | Dumesic et al. |
| 2007/0215300 | A1 | 9/2007 | Upfal et al. |
| 2008/0033187 | A1* | 2/2008 | Zhao et al. ..................... 549/489 |
| 2008/0033188 | A1 | 2/2008 | Dumesic et al. |
| 2008/0185112 | A1 | 8/2008 | Argyropoulos |
| 2008/0190013 | A1 | 8/2008 | Argyropoulos |
| 2008/0227162 | A1 | 9/2008 | Varanasi et al. |
| 2009/0020112 | A1 | 1/2009 | Massonne et al. |
| 2009/0062524 | A1 | 3/2009 | Massonne et al. |
| 2009/0084509 | A1 | 4/2009 | Luo et al. |
| 2009/0088564 | A1 | 4/2009 | Luo et al. |
| 2009/0124839 | A1 | 5/2009 | Dumesic et al. |
| 2009/0198046 | A1 | 8/2009 | Fanselow et al. |
| 2009/0242414 | A1 | 10/2009 | Welz-Biermann et al. |
| 2009/0255171 | A1 | 10/2009 | Dumesic et al. |
| 2010/0324310 | A1 | 12/2010 | Dumesic et al. |

FOREIGN PATENT DOCUMENTS

| | | |
|---|---|---|
| CN | 101289817 | 10/2008 |
| EP | 1 860 201 | 11/2007 |
| FR | 2663933 A1 | 1/1992 |
| FR | 2664273 A1 | 1/1992 |
| FR | 2669635 A1 | 5/1992 |
| GB | 591858 | 9/1947 |
| GB | 600871 | 4/1948 |
| GB | 876463 | 9/1961 |
| JP | 2005232116 | 9/2005 |
| JP | 2006223152 A | 8/2006 |
| WO | WO 92/10486 | 6/1992 |
| WO | WO 03/029329 | 4/2003 |
| WO | WO 2005/017001 | 2/2005 |
| WO | WO 2005/018799 | 3/2005 |
| WO | WO 2007/112090 | 10/2007 |
| WO | WO 2007/138256 | 12/2007 |
| WO | WO 2007/146636 | 12/2007 |
| WO | WO 2008/098032 | 8/2008 |
| WO | WO 2008/098036 | 8/2008 |
| WO | WO 2008/112291 | 9/2008 |
| WO | WO 2008/119770 | 10/2008 |
| WO | WO 2009/024607 | 2/2009 |

(Continued)

OTHER PUBLICATIONS

Seri et al. Chemistry Letters 2000, pp. 22-23.*

(Continued)

*Primary Examiner* — Layla Bland
(74) *Attorney, Agent, or Firm* — Lathrop & Gage LLP

(57) ABSTRACT

A method for converting a carbohydrate to a furan in a polar aprotic solvent in the presence of a chloride, bromide, or iodide salt or a mixture thereof and optionally in the presence of an acid catalyst, a metal halide catalyst and/or an ionic liquid (up to 40 wt %). The method can be employed in particular to produce furfural or 5-hydroxymethylfurfural.

14 Claims, 6 Drawing Sheets

(56) References Cited

FOREIGN PATENT DOCUMENTS

| WO | WO 2009/030512 | 3/2009 |
|---|---|---|
| WO | WO 2009/030949 | 3/2009 |
| WO | WO 2009/030950 | 3/2009 |
| WO | WO 2009/047023 | 4/2009 |
| WO | WO 2009/155297 | 12/2009 |

OTHER PUBLICATIONS

Zhao et al. Science, vol. 316, Jun. 15, 2007, pp. 1597-1600.*
JP2006223152A, Aug. 31, 2006, machine translation.*
Harris et al. J. Org. Chem., vol. 39, No. 5, 1974.*
Hayes et al. Biorefineries—Industrial Processes and Products, 2006, pp. 139-164.*
Roman-Leshkov et al. Nature, vol. 447, 21, Jun. 2007, 982-986.*
Fort et al. Green Chem., 2007, 9, 63-69.*
Adkins (1937) "Reactions of Hydrogen with Organic Compounds Over Copper-Chromium Oxide and Nickel Catalysis," University of Wisconsin Press: Madison, WI.
Ahmad et al. (Oct. 1995) "The formation of 2-furaldehyde and formic acid from pentoses in slighlty acidic deuterium oxide studied by 1H NMR spectroscopy," *Carbohydrate Research* :276, 309-320.
Amarasekara et al. (Web Release Oct. 26, 2009) "Hydrolysis and Decomposition of Cellulose in Brönsted Ionic Liquids Under Mild Conditions," *Ind. Eng. Chem. Res.* 48:10152-10155.
Angyal, S. J.(Oct. 1994) "The composition of reducing sugars in dimethyl sulfoxide solution." *Carbohydrate Res.* 263:1-11.
Angyal, S. J. (Jun. 1976) "Conformational Analysis in Carbohydrate Chemistry. III—The 13C N.M.R. Spectra of the Hexuloses," *Australian Journal of Chemistry* 29, 1249-1265.
Antal, Jr. et al. (Sep. 18, 1991) "Mechanism of Formation of 2-Furaldehyde From D-xylose," *Carbohydrate Res.* 217:71-85.
Antal. Jr. et al. (May 15, 1990) "Mechanism of Formation of 5-hydroxymethyl)-2-furaldehyde from D-Fructose and Sucrose," *Carbohydrate Res.* 199(1):91-109.
Benvenuti et al. (2000) "Heterogenous Zirconium and Titanium Catalysts for the Selective Synthesis of 5-Hydroxymethyl-2-Furaldehyde from Carbohydrates," *Appl. Catal. A. Gen.* 193:147-153.
Bicker et al. (Web Release Feb. 2003) "Dehydration of Fructose to 5-Hydroxymethylfurfural in Sub- and Supercritical Acetone," *Green Chem.* 5:280-284.
Binder et al. (Mar. 2010) "Fermentable Sugars by Chemical Hydrolysis of Biomass," *Proc. Nat. Acad. Sci. USA* 107(10):4516-4521.
Binder J.B. et al. (Sep. 2009) "Reactions of lignin model compounds in ionic liquids," *Biomass and Bioenergy* 33(9):1122-11303.
Binder et al. (Jan. 2009) "Simple Chemical Transformation of Lignocellulosic Biomass into Furans for Fuels and Chemicals," *J. Amer. Chem. Soc.*131:1979-1985, published on web Jan. 21, 2009.
Blazej et al. (1985) "Degradation reactions of cellulose and lignocellulose," In; *Cellulose and its Derivatives: Chemistry, Biochemistry, and Applications*, Kennedy, J. F., Phillips, G. O., Wedlock, D. J., Williams, P. A., Eds.; Ellis Horwood Ltd.: Chichester, England, 1985; pp. 97-117.
Brown et al. (1982) "Dehydration Reactions of Fructose in Non-Aqueous Media," *J. Chem. Technol. Biotechnol.* 32:920-924.
Carlini et al. (2004) "Selective Saccharides Dehydration to 5-Hydroxymethyl-2-Furaldehyde by Heterogenous Niobium Catalysis," *Appl. Catal. A Gen.* 183:295-302.
Carlini et al. (Web Release Sep. 2004) "Heterogeous Catalysts Based on Vanadyl Phosphate for Fructose Dehydration to 5-Hydroxymethyl-2-furaldehyde,"*Appl. Catal. A Gen.* 275:111-118.
Chheda et al. (Web Release Jan. 2007) "Production of 5-Hydroxymethylfurfural and furfural by dehydration of Biomass-Derived Mono- and Poly-Saccharides," *Green Chem.* 9:342-350, published on web Jan. 17, 2007.
Chheda et al. (Sep. 2007) "Liquid-phase catalytic processing of biomass-derived oxygenated hydrocarbons to fuels and chemicals," *Angew. Chem. Int. Ed.* 46:7164-7183.

Chheda et al. (Web Release Jan. 2007) "An Overview of Dehydration, Aldol Condensation and Hydrogenation Processes for Production of Liquid Alkanes from Biomass Derived Carbohydrates," *Catal. Today* 123:59-70.
Chiappe et al. (Web Release Sep. 2004) "Ionic liquids; solvent propertied and organic reactivity," *Phys. Org. Chem.*, 18:275-297, published online Sep. 21, 2004.
Chowdhury et al. (Mar. 2007) "Reactivity of Ionic Liquids," *Tetrahedron* 63:2363-2389, available online Dec. 8, 2006.
Cottier et al. (1991) "5-Hydrozymethylfurfural Syntheses and Chemical Transformations," *Trends Heterocycle. Chem.* 2:233-248.
Dadgar et al. (1983) "The Production of Hydromethyl Furfural from Sawdust," *Biotechnol. Bioeng. Symp.* 13:41-52.
Defaye et al. (Feb. 1985) "The Behaviour of D-Fructose and Inulin Towards Anhydrous Hydrogen Fluoride," *Carbohydrate Res.* 136:53-65.
Dias et al. (Apr. 2005) "Dehydration of Xyose into Furfural Over Micro-Mesoporous Sulfonic Acid Catalysts," *J. Catalysis* 229:414-423.
Dias et al. (Apr. 2007) "Modified Versions of Sulfated Zirconia as Catalysts for the Conversion of Xylose to Furfural," *Catal. Lett.* 114(3-4):151-160.
Ebner et al. (Oct. 2008) "Side reaction of cellulose with common 1-alkyl-3-methylimidazolium-based ionic liquids," *Tetrahedron Lett.* 49:7322-7324, available online Oct. 17, 2008.
El Hajj et al. (1987) "Synthase de l'hydroxymethyl-5 Furanne Carboxaldehyde-2 et de ses Derives pat Traitement Acide de sucres sur Resines Echangeuses d'ions," *Bulletin de la Societe Chimique de France* 5:855-860.
El Seoud et al. (Sep. 2007) "Applications of ionic liquids in carbohydrate chemistry: A window of opportunities," *Biomacromolecules* 8:2629-2647.
Fort et al. (May 2007) "Can Ionic Liquids Dissolve Wood? Processing and Analysis of Lognocellulosic Materials with 1-n-butyl-3-methylimidazolium Chloride," *Green Chem.* 9:63-69, published on web Oct. 17, 2006.
Garegg et al. (May 1988) "Hydrolysis of Glycosides Under Reducing Conditions," *Carbohydrate Res.* 176(1):145-148.
Gaset et al. (Apr. 1981) "Recent Developments in Processes for Obtaining 5-Hydroxymethyl-2-furancarboxaldehyde," *Informations Chimie* 212:179-184.
Girisuta et al. (Web Release Feb. 2007) "Kinetic Study on the Acid Catalyzed Hydrolysis of Cellulose to Levulinic Acid," *Ind. Eng. Chem. Res.* 46(6):1696-1708.
Halliday et al. (Web Release May 9, 2003) "One-Pot, Two-Step, Practical Catalytic Synthesis of 2,5-Diformylfuran from Fructose," *Org. Lett.* 5(11):2003-2005.
Harris et al. (Feb. 1960) "Preparation and Properties of Hydroxymethylfurfural," *Forest Products J.* 10:125-128.
Hermanutz et al. (Dec. 2006) "New developments in the manufacture of cellulose fibers with ionic liquids," *Chem. Fibers Int.* 6:342-343.
Huber et al. (Jun. 3, 2005) "Production of Liquid Alkanes by Aqueous-Phase Processing of Biomass-Derived Carbohydrates," *Science* 308:1446-1450.
International Search Report and Written Opinion, Corresponding to International Application No. PCT/US09/47547, Mailed Sep. 9, 2009.
Kumar et al. (Web Release Mar. 2009) "Methods for Pretreatment of Lignocellulosic Biomass for Efficient Hydrolysis and Biofuel Production," *Indus Eng. Chem. Res.* 48:3713-3729.
Kunkes et al. (Oct. 2008) "Catalytic conversion of biomass to monofunctional hydrocarbons and targeted liquid-fuel classes," *Science* 322:417-421.
Kuster, B.M.F. (1990) "Hydroxymethylfurfural (HMF). A Review Focusing on its Manufacture," *Starch* 42:314-321.
Lansalot-Matras et al. (Web Release Sep. 2003) "Dehydration of fructose into 5-hydroxymethylfurfural in the presence of ionic liquids," *Catal. Commun.* 4:517-520.
Lange et al. (Web Release Jul. 2007) "Lignocellulose conversion: An introduction to chemistry, process and economics," *Biofuels Bioprod. Bioref.* 1:39-48, published online Jul. 18, 2007.

(56) References Cited

OTHER PUBLICATIONS

Lewkowski, J. (Web Release Aug. 8, 2001) "Synthesis, Chemistry and Applications of 5-Hydroxymethylfurfural and Its Derivatives," *ARKIVOC* (i):17-54.
Li et al. (Aug. 2007) "Efficient acid-catalyzed hydrolysis of cellulose in ionic liquid," *Adv. Synth. Catal.* 349:1847-1850.
Li et al. (Web Release Dec. 2008) "Acid in ionic liquid: An efficient system for hydrolysis of lignocellulose," *Green Chem.* 10:177-182, published on web Dec. 17, 2007.
Lichtenthaler (Web Release May 7, 2002) "Unsaturated O- and N-Heterocycles from Carbohydrate Feedstocks," *Acc. Chem. Res.* 35(9):728-737.
Mamman et al. (Sep./Oct. 2008) "Furfural: Hemicellulose/xylose derived Biochemical," *Biofuels Bioproducts Biorefining* 2(5):438-454.
Mansilla et al. (Dec. 1998) Acid-catalysed hydrolysis of rice hull: Evaluation of furfural production, *Biosource Technol.* 66:189-193.
Marzialetti et al. (Aug. 2008) "Dilute acid hydrolysis of loblolly pine: a comprehensive approach," *Ind. Eng. Chem. Res.* 47:7131-7140, published on web Aug. 26, 2008.
Mascal et al. (Sep. 2008) "Direct, High-Yield Conversion of Cellulose into Biofuel," *Angew. Chem. Int. Ed.* 47:7924-7926.
McCormick (Dec. 1985) "Solution Studies of Cellulose in Lithium Chloride and N,N-Dimethylacetamide," *Macromolecules* 18(12):2394-2401.
Mercadier et al. (Jan. 1981) "Synthesis of 5-Hydroxymethyl-2-Furancarboxaldehyde Catalysed by Cationic Exchange Resins. Part 1. Choice of the Catalyst and the Characteristics of the Reaction Medium," *J. Chem. Tech. Biotechnol.* 31:489-496.
Moreau et al. (Feb. 2004) "Recent Catalytic Advances in the Chemistry of Substituted Furans from Carbohydrates and in the Ensuing Polymers," *Topics Catalysis* 27:11-30.
Moreau et al. (Jul. 2006) "Dehydration of Fructose and Sucrose into 5-Hydroxymethylfurfural in the Presence of 1-H-3-Methyl Imidazolium Chloride Acting Both as Solvent and Catalyst," *J. Mol. Catal. A: Chem.* 253(1-2):165-169.
Moreau et al. (Jan. 1998) "Selective Preparation of Furfural from Xylose Over Microporous Solid Acid Catalysts," *Ind. Crops Products* 7(2-3):95-99.
Moye, C.J. (1964) "Hydroxymethylfurfural," *Rev. Pure Appl. Chem.* 14:161-170.
Musau et al. (May 1987) "The Preparation of 5-Hydroxymethyl-2-Furaldehyde (HMF) from D-Fructose in the Presence of DMSO," *Biomass* 13:67-74.
Nakamura et al. (Dec. 1980) "The Dehydration of D-Fructose to 5-Hydroxymethyl-2-Furaldehyde," *Bull. Chem. Soc. Jpn.* 53:3705-3706.
Nimlos et al. (Web Release Oct. 4, 2006) "Energetics of Xylose Decomposition as Determines Using Quantum Mechanic Modeling," *J. Phys. Chem. A* 110(42):11824-11838.
Osada et al. (Web Release Dec. 2004) Low Temperature Catalytic Gasification of Lignin and cellulose with a Ruthenium Catalyst in Supercritical Water, 18, 327-333, published on web Dec. 5, 2003.
Poncini et al. (Dec. 1980) "Thermolysis of Sucrose in Dimethyl Sulphoxide Solution," *Carbohydrate Res.* 87(2):209-217.
Potthast et al. (Mar. 2002) "The Cellulose Solvent System N,N-dimethylacetamide/Lithium Chloride Revisited: The Effect of Water on Physiocichemical Properties and Chemical Stability," *Cellulose* 9(1):41-53.
Potthast et al. (Oct. 2002) "Degradation of Cellulosic Materials by Heating in DMAc/LiCl," *Tetrahedron Lett.* 43(43):7757-7759.
Potthast et al. (Jan. 2003) "Hydrolytic Processes and Condensation Reactions in the Cellulose Solvent System N,N-dimethylacetamide/Lithium Chloride. Part 2: Degradation of Cellulose," *Polymer* 44(1):7-17.
Pu et al. (Jan. 2007) "Ionic Liquid as a Green Solvent for Lignin," *J. Wood Chem. Technol.* 27(1):23-33.

Rigal et al. (Dec. 1981) "Selective Conversion of D-Fructose to 5-Hydroxymethyl-2-Furancarboxadehyde Using a Water-Solvent Ion-Exchange Resin Triphasic System," *Ind. Eng. Chem. Prod. Res. Dev.* 20(4):719-721.
Rinaldi et al. (Sep. 2008) "Depolymerization of cellulose using solid catalysts in ionic liquids," *Angew. Chem. Int. Ed.* 47:8047-8050.
Robinson et al. (Web Release Nov. 19, 2003) "The Use of Catalytic Hydrogenation to Intercept Carbohydrates in a Dilute Acid Hydroluluusis of Biomass to Effect a Clean Separation from Lignin," *Biomass. Bioeng.* 26(5):473-483.
Román-Leshkov et al. (Jun. 2006) "Phase Modifiers Promote Efficient Production of Hydroxymethylfurfural from Fructose," *Science* 312:1933-1937.
Román-Leshkov et al. (Jun. 2007) "Production of Dimethylfuran for Liquid Fuels from Biomass-Derived Carbohydrates," *Nature* 447:982-986.
Seri et al. (Jan. 2000) "Highly Efficient Catalytic Activity of Lanthanide(III) Ions for Conversion of Saccharides to 5-Hydroxymethyl-2-furfural in Organic Solvent," *Chem. Lett.* 22-23.
Seri et al. (2001) "Catalytic Activity of Lanthanide(III) Ions for the Dehydration of Hexose to 5-Hydroxymethyl-2-furaldehyde in Water," *Bull. Chem. Soc. Jpn.* 74(6):1145-1150.
Sievers et al. (Web Release Jan. 2009) "Ionic-liquid—phase hydrolysis of pine wood," *Ind. Eng. Chem. Res.* 48(3):1277-1286.
Sproull et al. (Jun. 1985) "Production of Furfural from Corn Stover Hemicellulose," *Biotechnol. Bioeng. Symp.* 15:561-577.
Srokol et al. (Apr. 2004) "Hydrothermal upgrading of biomass to biofuel; studies on some monosaccharide model compounds," *Carbohydrate Res.* 339:1717-1726.
Swatloski et al. (Apr. 2002) "Dissolution of Celluose with Ionic Liquids," *J. Amer. Chem. Soc.* 124:4974-4975.
Szmant et al. (Jan. 1981) "The Preparation of 5-Hydroxtmethlfurfuraldehyde from High Fructose Corn Syrup and Other Carbohydrates," *J. Chem. Technol. Biotechnol.* 31:135-145.
Tyrlik et al. (Apr. 1996) "Concentrated Water Solutions of Salts as Solvents for Reaction of Carbohydrates. Part 2. Influence of Some Magnesium Salts and Some Ruthenium Species on Catalysts of Dehydration of Glucose," *J. Mol. Catal. A. Chem.* 106(3):223-233.
Van Dam et al. (Mar. 1986) "The Conversion of Fructose and Glucose in Acidic Media: Formation of Hydroxymethylfurfural," *Starch* 38:95-101.
Van Haveren et al. (Jan. 2008) Bulk chemicals from biomass. *Biofuels Bioprod. Bioref.* 2:41-57, published on line Dec. 19, 2007.
Vanoye et al. (Jan. 2009) "Kinetic model for the hydrolysis of lignocellulosic biomass in the ionic liquid, 1-ethyl-3-methyl-imidazolium chloride," *Green Chem.* 11:390-396.
Vitz et al. (Jan. 2009) "Extended dissolution studies of cellulose in imidazolium based ionic liquids," *Green Chem.* 11:417-424.
Yong et al. (Nov. 2008) "Efficient Catalytic System for the Selective Production of 5-Hydroxymethylfurfural from Glucose and Fructose," *Angew. Chemie Int. Ed.* 47:9345-9348.
Zhang et al. (Mar. 2010) "Ionic Liquid—Water Mixtures: Enhanced Kw for Efficient Cellulosic Biomass Conversion," *Energy Fuels* 24, 2420-2417.
Zhang et al. (Jun. 2007) "Fractionating Recalcitrant Lignocellulose at Modest Reaction Conditions," *Biotechnol. Bioeng.* 97(2):214-223.
Zhao et al. (Jun. 2007) "Metal Chlorides in Ionic Liquid Solvents Convert Sugars to 5-Hydroxymethylfurfural," *Science* 316:1597-1600.
Zhu et al. (Mar. 2006) "Dissolution of cellulose with ionic liquids and its application: A mini-review," *Green Chem.* 8:325-327.
Extended European Search Report issued Oct. 24, 2011 in corresponding EP application 09767606.8; PCT Regional Stage of PCT/US2009047547.
Wang et al. (Oct. 2010) "The application of ionic liquids in dissolution and separation of lignocellulose" in *Clean Energy Systems and Experiences* (ed. K. Eguchi), Sciyo.com (www.sciyo.com), India, publisher, Chapter 4, pp. 71-84; available on-line at <http://cdn.intechopen.com/pdfs/11933/InTech-The_application_of_ionic_liquids_in_dissolution_and_separation_of_lignocellulose.pdf>.

* cited by examiner

CHEMICAL TRANSFORMATION OF LIGNOCELLULOSIC BIOMASS INTO FUELS AND CHEMICALS

CROSS-REFERENCE TO RELATED APPLICATIONS

This application is a continuation of U.S. patent application Ser. No. 12/485,755, filed Jun. 16, 2009, which claims the benefit of U.S. provisional application 61/073,285, filed Jun. 17, 2008. Each of these applications is incorporated by reference in its entirety herein.

U.S. GOVERNMENT SUPPORT

This invention was made with government support under NIH GM044783 awarded by the National Institutes of Health. The government has certain rights in the invention.

FIELD OF THE INVENTION

The present invention relates to methods for chemical transformation of sugars and cellulosic biomass into fuels and chemicals in substantial yields under moderate conditions.

BACKGROUND OF THE INVENTION

Readily available from crop residues and forests, cellulosic biomass is a largely untapped resource for fuels and chemicals. [Perlack et al., "Biomass as Feedstock for a Bioenergy and Bioproducts Industry: The Technical Feasibility of a Billion-Ton Annual Supply," U.S. Department of Energy and U.S. Department of Agriculture, Oak Ridge National Laboratory: Oak Ridge, Tenn. DOE/GO-102995-2135 (2005).] Efficient transformations of biomass polymers into small molecules will enable the development of a renewable chemical and fuel industry. [Werpy et al., "Top Value-Added Chemicals from Biomass, Volume I: Results of Screening for Potential Candidates from Sugars and Synthesis Gas," U.S. Department of Energy, Office of Scientific and Technical Information: Oak Ridge, Tenn. DOE/GO-102004-1992 (2004).] Useful small molecules that can be obtained from biomass include furans, such as 5-hydroxyfurfural and furfural.

A hexose dehydration product, 5-hydroxymethylfurfural (HMF), is a six-carbon molecule analogous to commodity chemicals like adipic acid and terephthalic acid. As shown in FIG. 1, HMF can be converted by straightforward methods into a variety of useful acids, aldehydes, alcohols, and amines, as well as the promising fuel, 2,5-dimethylfuran (DMF). [Lichtenthaler, Acc. Chem. Res. 35, 728-737 (2002); Lewkowski, ARKIVOC, 17-54 (2001).] The energy content of DMF (31.5 MJ/L) is similar to that of gasoline (35 MJ/L) and 40% greater than that of ethanol (23 MJ/L). [Nisbet, H. B. J. Inst. Petrol. 1946, 32, 162-166; Roman-Leshkov, Y.; Barrett, C. J.; Liu, Z. Y.; Dumesic, J. A. Nature 2007, 447, 982-986.] Moreover, DMF (bp 92-94° C.) is less volatile than ethanol (bp 78° C.) and is immiscible with water making DMF an attractive alternative liquid fuel for transportation.

HMF synthesis has been demonstrated in water [Lewkowski, ARKIVOC, 17-54 (2001).], traditional organic solvents [Halliday et al., Org. Lett. 5, 2003-2005 (2003)], multiphase systems [Roman-Leshkov et al., Science 312, 1933-1937 (2006); Chheda et al., Green Chemistry 9, 342-350 (2007).], and ionic liquids [Zhao et al., Science 316, 1597-1600 (2007); Moreau et al., J. Mol. Catal. A: Chem. 253, 165-169 (2006); Moreau et al., Catal. Commun. 4, 517-520 (2003).]. In a typical process, acid catalysts are used to dehydrate fructose to make HMF as shown in FIG. 2. This figure also schematically illustrates the potential for formation of undesired side-products and that HMF itself can be further degraded.

Nevertheless, several underlying factors have blocked the economical production of HMF and HMF-derivatives for over a century: the requirement for expensive fructose feedstock, the low selectivity of fructose dehydration in water, and the difficulty of purifying HMF from the few suitable organic solvents in which the process can be conducted.

High HMF yields (up to 85% molar yield) from fructose are reported for mixed aqueous-organic biphasic systems containing polar organic solvents [Roman-Leshkov et al., Science 312, 1933-1937 (2006); Chheda et al., Green Chemistry 9, 342-350 (2007); Dumesic et al., published application US 2008/0033188 (2008)]. This work describes a biphasic reaction process for making furan derivatives involving dehydrating a feedstock solution containing a carbohydrate in the presence of an acid catalyst. The reaction is conducted in a reaction vessel containing a biphasic reaction medium containing an aqueous reaction solution and a substantially immiscible organic extraction solution. The biphasic medium contains a modifier in the aqueous phase, in the organic phase or both to improve selectivity of the process to yield furan derivative compounds. The aqueous phase modifier can be a metal salt, such as NaCl or a dipolar aprotic species including dimethylsulfoxide, dimethylformamide, N-methylpyrrolidinone, acetonitrile, butryolactone, dioxane or pyrrolidinone. Catalysts reported include HCl, $H_2SO_4$, and $H_3PO_4$. Although high molar yields are reported for conversion of fructose to HMF, the highest yields from glucose do not exceed 30% and conversion of cellulose to HMF is not reported. The patent application also reports conversion of HMF to DMF using $CuCrO_4$ or Cu:Ru on carbon.

Other recent reports describe conversion of fructose, glucose, and cellulose into HMF in ionic liquids [Zhao et al., Science 316, 1597-1600 (2007); Zhao et al., published application US 2008/0033187 (2008)]. Zhao et al. report a method for conversion of a carbohydrate in an ionic liquid producing a furan at a substantial yield. The method involves mixing carbohydrate up to the limit of solubility with the ionic liquid, and heating the carbohydrate in the presence of a catalyst at a reaction temperature and for a reaction time sufficient for conversion to furan at a substantial yield. Exemplary ionic liquids are [EMIM]Cl (1-ethyl-3-methyl-imidazolium chloride) and [BMIM]Cl (1-butyl-3-methyl-imidazolium chloride). The reference reports conversion of fructose to HMF in ionic liquid in the presence of metal halides and acid catalysts and the conversion of glucose to HMF in ionic liquid in the presence of chromium chloride catalyst. Ionic liquids are expensive, and product is difficult to purify.

In the past, monosaccharides such as fructose and glucose have been the primary feedstocks for synthesis of HMF. Polysaccharides such as cellulose are another type of feedstock for HMF synthesis which are readily and inexpensively available. Despite this potential, HMF is not typically obtained from cellulose in high yield. Aqueous acid and high temperatures and pressures (250-400° C., 10 MPa) enable conversion of cellulose into HMF and levulinic acid with a 30% molar yield of HMF [Kono et al., published application Jap. 2005232116 (2005)]. In alkylimidazolium chloride ionic liquids, chromium chlorides are reported to catalyze the conversion of cellulose into HMF in 51% molar yield [Zhao et al., published application US 2008/0033187 (2008)]. The first method requires harsh conditions which increase process costs, and the second method uses expensive ionic liquid solvents.

Most efforts toward HMF production have used edible starting materials, primarily fructose and glucose. In fact, almost all renewable fuels and chemicals are usually based on food resources such as starch, sugars, and oils. These simple starting materials are relatively easy to convert into valuable products, while inedible lignocellulosic biomass is relatively recalcitrant and heterogeneous, making its conversion typically inefficient and uneconomical. [Zhang, Y.-H. P.; Ding, S.-Y.; Mielenz, J. R.; Cui, J.-B.; Elander, R. T.; Lasser, M.; Himmel, M. E.; McMillan, J. R.; Lynd, L. R. Biotechnol. Bioeng. 2007, 97, 214-223.]

Both xylan and xylose can be dehydrated into furfural, a biofuel precursor and industrial chemical. [Zeitsch, K. J. (2000) The Chemistry and Technology of Furfural and Its Many By-Products Elsevier: Amsterdam; Lee, J.-M.; Kim, Y.-C.; Hwang, I. T.; Park, N.-J.; Hwang, Y. K.; Chang, J.-S. (2008) Biofuels, Bioproducts, and Biorefining, 2, 438-454.] Furfural is perhaps the most common industrial chemical derived from lignocellulosic biomass with annual production of more than 200,000 t. [Kamm, B.; Gruber, P. R.; Kamm, M., Eds (2006) Biorefineries—Industrial Processes and Products, Wiley—VCH: Weinheim, Germany.] The conversion of pentoses into furfural has been reported. [Sproull, R. D.; Bienkowski, P. R.; Tsao, G. T. (1985) Biotechnology and Bioengineering Symposium, 15, 561-577; Moreau, C.; Durand, R.; Peyron, D.; Duhamet, J.; Rivalier, P. (1988) Industrial Crops and Products, 7, 95-99; Mansilla, H. D.; Baeza, J.; Urzua, S.; Maturana, G.; Villasenor, J.; Duran, N. (1998) Bioresource Technology 66, 189-193; Dias, A. S.; Lima, S.; Pillinger, M.; Valente, A. A. (2007) Catalysis Letters, 114, 151-160.] Most industrial processes achieve yields in the range of 50 molar %, which may be limited by homopolymerization and condensation with unreacted xylose. In typical processes reported, Brønsted acidic catalysts were used in aqueous solution at temperatures greater than 150° C. [Moreau, C.; Durand, R.; Peyron, D.; Duhamet, J.; Rivalier, P. (1998) Industrial Crops and Products, 7, 95-99; Dias, A. S.; Lima, S.; Pillinger, M.; Valente, A. A. (2007) Catalysis Letters, 114, 151-160.] FIG. 3 illustrates mechanisms proposed for the formation of furfural from xylan (A) and xylose (B). In this mechanism, the C-2 hydroxyl group is displaced to form a xylose-2,5-anhydride and subsequent dehydration steps produce furfural. [Antal, M. J.; Richards, G. N. (1991) Carbohydrate Research 217, 71-85; Nimlos, M. R.; Qian, X.; Davis, M.; Himmel, M. E.; Johnson, D. K. (2006) Journal of Physical Chemistry A 110, 11824-11838.]

There remains a need in the art for efficient and lower cost methods for conversion of biomass, including lignocellulosic biomass, to useful fuels and chemicals. This invention provides methods for conversion of biomass to furans, particularly to HMF and furfural, and to the potentially important fuel component, DMF (2,5-dimethylfuran) which employ polar aprotic solvents in the presence of certain salts.

SUMMARY OF THE INVENTION

The present invention provides a method for converting a carbohydrate to a furan in a polar aprotic solvent in the presence of a chloride, bromide, or iodide salt or a mixture thereof and optionally in the presence of an acid catalyst, a metal halide catalyst or an ionic liquid (up to 40 wt %). In a. specific embodiment the furan is HMF. In another embodiment the furan is furfural.

In a specific embodiment, the invention provides a process for preparing HMF by heating a mixture of a carbohydrate, an organic solvent, a halide salt and optionally a metal catalyst as illustrated in FIG. 3. In a more specific embodiment, the halide salt is a chloride, bromide, or iodide salt or mixtures thereof. Yet more specifically, the organic solvent is DMA (N,N-dimethylacetamide) the chloride salt is LiCl, and the metal catalyst is a chromium catalyst, particularly $CrCl_2$ or $CrCl_3$. Yet more specifically, the solvent is DMA-LiCl having from 0.5 wt % to 20 wt % LiCl. Yet more specifically the reaction is heated to 80 to 140° C., and more specifically to about 120° C., for 1 hour to 1 day to produce HMF. In a related embodiment, furfural can be formed by an analogous process under analogous conditions using analogous solvents and reagents from a carbohydrate feedstock containing 5-carbon sugars, e.g., xylose or xylan. In a related embodiment, a combination of HMF and furfural can be formed by analogous processes under analogous conditions using analogous solvents and reagents from a carbohydrate feedstock containing both 6-carbon sugars and 5-carbon sugars.

It is specifically noted that the reaction system employed in this invention for conversion of carbohydrates to furfural or HMF is not a biphasic system. Conversion reactions of HMF and or furfural to other products may be conducted in a biphasic solution, if appropriate or useful. In a specific embodiment, the furan produced in the reaction is a furan other than a halogenated furan. In a specific embodiment, the furan produced in the reaction is a furan other than 5-chloromethylfurfural.

In another aspect, the invention provides a method for making DMF which comprises, as a first step, making HMF by a method of this invention from a carbohydrate or carbohydrate feedstock and thereafter converting HMF to other useful fuels or chemicals, particularly DMF. In a specific embodiment, HMF is converted to DMF via hydrogenolysis. HMF can be converted to other useful species as is known in the art and as illustrated in FIGS. 1-3. In a more specific embodiment, hydrogenolysis is conducted employing a copper catalyst and particularly using a copper-ruthenium catalyst or a copper chromite catalyst. Specific useful catalysts include $Cu/Cr_2O_3$ with optional promoters including Ba and Cu:Ru/carbon catalysts.

In an additional aspect of the invention, the method herein for conversion of carbohydrates to furfural and/or HMF can be combined with any art-recognized process for further conversion of furfural or HMF into useful fuels or chemicals. Exemplary conversions of HMF are illustrated in FIG. 1.

In yet another aspect of the invention, the invention provides a method for making furan which comprises, as a first step, making furfural by a method of this invention from a carbohydrate or carbohydrate feedstock comprising 5-carbon sugars and thereafter converting furfural to furan. Furfural made by the methods herein can be converted to other useful fuels by methods that are known in the art. In a specific embodiment, furfural is converted to furan via decarbonylation by methods that are known in the art.

In specific embodiments, the carbohydrate is a monosaccharide, a disaccharide or a polysaccharide. In specific embodiments, the carbohydrate is sucrose, fructose, glucose, mannose, maltose, lactose, galactose, tagatose, psicose, sorbose, cellobiose, a mixture of any two or more thereof or a carbohydrate feedstock comprising one or more of the listed carbohydrates. In specific embodiments, the carbohydrate is cellulose. In specific embodiments, the carbohydrate feedstock is lignocellulosic biomass. In specific embodiments, the carbohydrate is a carbohydrate feedstock comprising cellulose. In specific embodiments, the carbohydrate feedstock is, among others, corn stover, poplar wood, switchgrass, Miscanthus giganteus, pine sawdust, simulated cane syrup, starch or mixtures thereof. In another embodiment, the carbohydrate is or comprises a 6-carbon sugar and the product is HMF. In another embodiment, the carbohydrate is or comprises a 5-carbon sugar and the product is furfural. Specific 5-carbon sugars include among others arabinose, xylose, ribose or xylose. In specific embodiments, the carbohydrate is combined with an amount of solvent effective to solubilize the carbohydrate. The amount of carbohydrate combined with the solvent ranges from greater than 0 wt % up to the solubility limit of the carbohydrate in the solvent. In specific embodiments, the amount of carbohydrate combined with the solvent ranges from 0.5 wt % to 25 wt %. In more specific embodiments, the amount of carbohydrate combined with the solvent ranges from 1 wt % to 20 wt %. In yet more specific embodiments, the amount of carbohydrate combined with solvent ranges from 5 wt % to 15 wt %.

In specific embodiments, the polar aprotic solvent employed in the methods herein is a N,N-dialkylacetamide, in particular N,N-dimethylacetamide (DMA) or N,N-diethylacetamide (DEA). In other embodiments, the solvent is a N,N-dialkylformamide, including dimethylformamide; a pyrrolidone (a 2-pyrrolidone or a 3-pyrrolidone), including an alkyl- or N-alkyl-substituted pyrrolidinone or more specifically including N-methylpyrrolidone, or 1-ethyl-2-pyrrolidinone; a dialkylsulfone, or more specifically methysulfonylmethane ($SO_2(CH_3)_2$) and including the cyclic sulfone, sulfolane, as well as alkyl or dialkyl sulfolanes and more specifically including sulfolane(tetramethylene sulfone) or 3-methylsulfolane; a dialkyl sulfoxide, particularly dimethylsulfoxide; an alkyl or N-alkyl substituted lactam, including N-methylcaprolactam; a dialkyl propionamide, including N,N-dimethylpropionamide; 1-pyrolidine carboxaldehyde; or miscible mixtures thereof. Preferred solvents include DMA and N-methylpyrrolidone. Acetonitrile and pyridine are not preferred solvents of this invention. Preferred solvents are anhydrous. In a specific embodiment, the solvent is not an ionic liquid. In a specific embodiment, the solvent does not contain an ionic liquid.

In specific embodiments, the concentration of chloride, bromide, or iodide in the solvent in the methods herein ranges from 0.5 wt % to the saturation concentration of the particular halide salt in the particular solvent, for example, at a concentration between 1.0 M and the saturation concentration of the salt in the particular solvent. In a specific embodiment, the concentration of the salt in the solvent can range from 0.5 wt % to 15 wt %, dependent upon the solvent. In another embodiment, the concentration of the salt in the solvent can range from 5 wt % to the saturation concentration of the salt in the particular solvent. In another specific embodiment, the concentration of the salt can range from 5 wt % to 15 wt %, dependent upon the solvent. In specific embodiments, the chloride salt is LiCl. In a specific embodiment, the concentration of LiCl ranges from 5 to 15 wt % dependent upon the solvent. In other specific embodiments, the chloride salt is NaCl or KCl. In other specific embodiments, the bromide salt is LiBr. In other specific embodiments, the bromide salt is NaBr. In other specific embodiments, iodide salt is LiI. In other specific embodiments, the iodide salt is NaI or KI. Fluoride salts are not preferred salts of this invention. In a specific embodiment, the salt is an alkali metal salt of $Cl^-$, $Br^-$ or $I^-$. In a specific embodiment, the salt is an alkali metal salt of $Cl^-$, or $Br^-$. In a specific embodiment, a mixture of chloride, bromide, or iodide salts can be employed. In a specific embodiment, a mixture of chloride, or bromide salts can be employed.

In specific embodiments, the reaction includes a catalyst. In more specific embodiments, the catalyst is a Bronsted acid or a metal halide or a mixture of such catalysts. In other embodiments, the acid is a mineral acid, including, among others, HCl, sulfuric acid, and nitric acid. In specific embodiments, the acid catalyst is present in the reaction mixture in a concentration ranging from 1 mol % to 10 mol %. In other embodiments, the metal halide is a metal chloride or a metal bromide. In other embodiments, the metal halide is selected from chlorides or bromides of aluminum, copper, chromium, iron, vanadium, molybdenum, palladium, platinum, ruthenium, rhodium, or mixtures thereof. In specific embodiments the catalyst is $CrCl_2$, $CrCl_3$, $CrBr_3$ or mixtures thereof.

In specific embodiments, up to 40 wt % of an ionic liquid is added to the reaction mixture. More specifically, the ionic liquid is present in an amount of 40 wt % or less. Yet more specifically, the ionic liquid is present in an amount ranging from 0.5 wt % to 40 wt %. In other embodiments, the ionic liquid is present in an amount of 20 wt % or less. More specifically, the ionic liquid is present in an amount ranging from 0.5 wt % to 20 wt %. An ionic liquid is a salt that melts near or below ambient room temperature. In specific embodiments, the ionic liquid is an alkylimidazolium ionic liquid, more particularly an alkylimidazolium halide ionic liquid. In other specific embodiments, the ionic liquid is an alkylimidazolium chloride ionic liquid. In more specific embodiments, the ionic liquid is [EMIM]Cl, [BMIM]Cl, [EMIM]Br, 1-ethyl-2,3-dimethylimidazolium chloride, or a mixture thereof. In specific embodiments, the ionic liquid is an alkylpyridinium ionic liquid, more particularly an alkylpyridinium halide ionic liquid. In more specific embodiments, the ionic liquid is 1-ethylpyridinium chloride, 1-butyl-4-methylpyridinium chloride, or a mixture thereof. Additional ionic liquids useful in this invention are provided in US 2008/0033187. In specific embodiments, the amount of ionic liquid added ranges from 5 wt % to 40 wt % or from 10wt % to 30 wt %. In other embodiments, the amount of ionic liquid is 30 wt % or less, 25 wt % or less, 20 wt % or less, 15 wt % or less or 10 wt % or less.

In specific embodiments, the reaction mixture includes a metal halide, particularly a metal chloride catalyst, and an ionic liquid. In other embodiments, the reaction mixture includes an acid catalyst and an ionic liquid. In specific embodiments, the reaction mixture does not contain an ionic liquid.

In specific embodiments, a cation complexing agent is added to the reaction mixture. In specific embodiments, the complexing agent complexes at least a portion of the cation of the chloride, bromide, or iodide salt or mixture thereof, which is added to the mixture of carbohydrate in polar aprotic solvent. In specific embodiments, the salt is an alkali metal salt or an alkaline earth metal salt. In specific embodiments, the complexing agent complexes at least a portion of the alkali metal or alkaline earth metal cation of the added salt. In specific embodiments, the complexing agent is a crown ether, an aza-crown, a mixed aza-crown ether, a cryptand, a podand, a calixarene, polyethylene glycol/polyethylene oxide or a mixture thereof. In more specific embodiments, the complexing agent is 12-crown-4,15-crown-5,18-crown-6, dibenzo-18-crown-6 or mixtures there of. In other more specific embodiments, the complexing agent is cyclen, cyclam or a mixture thereof. In other more specific embodiments, the complexing agent is 4, 13, diaza-18-crown-6. In specific embodiments, the complexing agent is [2.2.2] cryptand. In specific embodiments, the complexing agent is added to the reaction in an amount equimolar to the chloride, bromide or iodide salt added. In specific embodiments, the complexing agent is added to the reaction in an amount ranging from 10% less than equimolar to 10% more than equimolar to the chloride, bromide or iodide salt added.

In specific embodiments, the carbohydrate conversion reaction is carried out at ambient pressure and at temperatures ranging from 50 to 200° C. More specifically, the reaction is carried out at a temperature ranging from 80 to 140° C. or at a temperature between 80 and 120° C. In a specific embodiment, the reaction is carried out at a temperature ranging from ambient temperature to 150° C. In specific embodiments, the conversion reaction can be carried out at a pressure ranging from ambient to up to 5-fold higher or lower than ambient pressure.

In specific embodiments, the conversion reaction is carried out until the carbohydrate in the carbohydrate feedstock is consumed. In an alternative specific embodiment, the conversion reaction is carried out until a desired yield of product is achieved. In a specific embodiment, the conversion reaction is carried out until a maximal yield of HMF, furfural or a mixture thereof is achieved. More specifically the reaction can be carried out for hours, days or months. More specifically the reaction can be carried out in a batch or a continuous mode as is known in the art.

In specific embodiments, the furfural or HMF formed in the reaction herein is recovered from the reaction mixture by passage through a hydrated nonpolar resin, e.g., mixed bed ion exchange resin, eluting with aqueous alcohol, such as a mixture of n-butanol and methanol in water (e.g., a 1:2:7 mixture of n-butanol:methanol:water). In another embodiment, chloride, bromide or iodide salt is removed or its concentration decreased in the furfural or HMF product. More specifically chloride salt is substantially removed from product HMF or furfural to achieve a chloride concentration of 1 mM or less prior to further conversion of the HMF or furfural.

For example, the chloride salt, e.g., LiCl, is removed from the product solution (in polar aprotic solvent) by ion exclusion methods. Ion exclusion purification can, for example, be conducted with water elution using a Dowex 50WX8-200 resin in the form of the metal cation of the chloride salt, e.g., in the $Li^+$ form.

In another aspect of the invention, a method for solubilizing or dissolving a carbohydrate from biomass is provided. In a specific embodiment, the biomass is lignocellulosic biomass. In specific embodiments, the carbohydrate is cellulose and/or hemicellulose in biomass. In another specific embodiment, the biomass is corn stover, poplar wood or switch grass. In this method, biomass containing carbohydrate is contacted and mixed with a polar aprotic solvent in the presence of a chloride, bromide, or iodide salt or a mixture thereof. In specific embodiments, the chloride, bromide or iodide salt is an alkali metal salt or an alkaline earth metal salt. In specific embodiments, the chloride, bromide and/or iodide salt is present in the mixture at a total salt concentration of 0.5 wt % up to the saturation concentration of the salt or salts in the solvent or mixture thereof. In a specific embodiment, the concentration of the salt in the solvent can range from 0.5 wt % to 15 wt %, dependent upon the solvent employed. In another embodiment, the concentration of the salt in the solvent can range from 5 wt % to the saturation concentration of the salt in the particular solvent. In another specific embodiment, the concentration of the salt can range from 5 wt % to 15 wt %, dependent upon the solvent. In specific embodiments, the chloride salt is LiCl. In a specific embodiment, the concentration of LiCl ranges from 5 to 15 wt % dependent upon the solvent. In a specific embodiment, the concentration of LiCl ranges from 9 to 11wt %. In other specific embodiments, the chloride salt is NaCl or KCl. In other specific embodiments, the bromide salt is LiBr. In other specific embodiments, the bromide salt is NaBr. In other specific embodiments, iodide salt is LiI. In another specific embodiment, a catalyst is added to the mixture to generate glucose. In a more specific embodiment the catalyst is an acid catalyst. In yet more specific embodiments, the acid catalyst is a mineral acid, e.g., hydrochloric acid. In a specific embodiment the catalyst is a metal halide salt, e.g. copper(II) chloride. In a specific embodiment, the solubilizing or dissolving step is carried out at about room temperature. In another specific embodiment, the solubilization or dissolving step is carried out at a temperature ranging from ambient to 100° C. or from ambient to 80° C. In a specific embodiment, the solvent is a dialkylacetamide, in particular dimethylacetamide (DMA) or diethylacetamide (DEA). In a specific embodiment, the solvent is DMA containing LiCl (10 wt %). In a specific embodiment, the solubilization or dissolving step is carried out by stirring the components at a selected temperature for a time effective to solubilize or dissolve the carbohydrate. This effective time can range from one to several hours, to one to several days.

In a related embodiment, the invention provides a method for solubilizing cellulose or hemicellulose. In this method, cellulose and/or hemicellulose is contacted and mixed with a polar aprotic solvent in the presence of a chloride, bromide, or iodide salt or a mixture thereof. In specific embodiments, the chloride, bromide or iodide salt is an alkali metal salt or an alkaline earth metal salt. In specific embodiments, the chloride, bromide and/or iodide salt is present in the mixture at a total salt concentration of 0.5 wt % up to the saturation concentration of the salt or salts in the solvent or mixture thereof. In a specific embodiment, the concentration of the salt in the solvent can range from 0.5 wt % to 15 wt %, dependent upon the solvent employed. In another embodiment, the concentration of the salt in the solvent can range from 5 wt % to the saturation concentration of the salt in the particular solvent. In another specific embodiment, the concentration of the salt can range from 5 wt % to 15 wt %, dependent upon the solvent. In specific embodiments, the chloride salt is LiCl. In a specific embodiment, the concentration of LiCl ranges from 5 to 15 wt % dependent upon the solvent. In a specific embodiment, the concentration of LiCl ranges from 9 to 11 wt %. In a specific embodiment, the salt is a chloride, bromide or iodine salt other than LiCl. In other specific embodiments, the chloride salt is NaCl or KCl. In other specific embodiments, the bromide salt is LiBr. In other specific embodiments, the bromide salt is NaBr. In other specific embodiments, iodide salt is LiI. In another specific embodiment, a catalyst is added to the mixture to generate glucose. In a more specific embodiment the catalyst is an acid catalyst. In yet more specific embodiments, the acid catalyst is a mineral acid, e.g., hydrochloric acid. In a specific embodiment the catalyst is a metal halide salt, e.g. copper(II) chloride. In a specific embodiment, the solubilizing or dissolving step is carried out at about room temperature. In another specific embodiment, the solubilization or dissolving step is carried out at a temperature ranging from ambient to 100° C. or from ambient to 80° C. In a specific embodiment, the solvent is a dialkylacetamide, in particular dimethylacetamide (DMA) or diethylacetamide (DEA). In a specific embodiment, the solvent is DMA containing LiCl (10 wt %). In a specific embodiment, the solubilization or dissolving step is carried out by stirring the components at a selected temperature for a time effective to solubilize or dissolve the carbohydrate. This effective time can range from one to several hours, to one to several days.

In another related aspect, the invention provides a method for generating one or more monosaccharides from a material containing cellulose or from biomass which comprises the step of contacting the biomass with a polar aprotic solvent containing a chloride, bromide or iodide salt to solubilize or dissolve carbohydrate of material containing cellulose or the biomass. In a specific embodiment, the biomass is lignocellulosic biomass. In a specific embodiment, the monosaccharide is glucose. In a specific embodiment, the solvent is DMA. In a specific embodiment, the salt is LiCl. In a specific embodiment, the monosaccharide is generated as a component in the polar aprotic solvent mixture. In another embodiment, the solvent contains a mixture of chloride, bromide, or iodide salts. In another embodiment, the biomass is contacted with a polar aprotic solvent containing a chloride, bromide or iodide salt and a catalyst. In a specific embodiment the catalyst is an acid, such as a mineral acid, e.g., hydrochloric acid. In a specific embodiment the catalyst is a metal halide salt, e.g. copper(II) chloride. The monosaccharide can be isolated, if desired, and further purified, if desired from the solvent mixture. More specifically, the salt can be removed from the mixture containing the solvent and monosaccharide. More specifically, the monosaccharide can be isolated from the salt and the solvent.

Mixtures of monosaccharide in polar aprotic solvents containing a chloride, bromide or iodide salt of this invention formed by the solubilizing or dissolving step contain glucose or other monosaccharide(s) and can be employed as a feedstock containing glucose or other monosaccharide for any purpose. In specific embodiments, the mixture is acidic. In specific embodiments, the mixture has pH less than 5, less than 3 or less than 1. In other embodiments, the mixture contains a metal halide salt, e.g. copper(II) chloride. Monosaccharide, particularly glucose, can be isolated and purified, if desired, from these mixtures by methods that are well-known in the art to provide the monosaccharide(s), including glucose, for any purpose. The solubilizing or dissolving method of this invention allows the generation of a monosaccharide or mixture of monosaccharides, particularly glucose or a mixture of glucose with one or more other monosaccharides, from a more complex carbohydrate or from various forms of biomass.

The invention also provides a monosaccharide feedstock comprising a monosaccharide in a polar aprotic solvent and a chloride, bromide or iodide salt. In a specific embodiment, the polar aprotic solvent is DMA. In an embodiment, the salt is present in an amount ranging from 0.5 wt % to 20 wt %. In a more specific embodiment, the salt is present in an amount ranging from 5 wt % to 15 wt %. In a more specific embodiment, the salt is present in an amount ranging from 9 wt % to 11 wt %. In a specific embodiment, the monosaccharide is glucose. In a specific embodiment, the feedstock further comprises lignin. The feedstock can be employed as a source of the monosaccharide for any application.

Additional aspects of the invention can be ascertained on review of the Figures, following Detailed Description and the Examples.

DETAILED DESCRIPTION OF THE INVENTION

Figure 1:
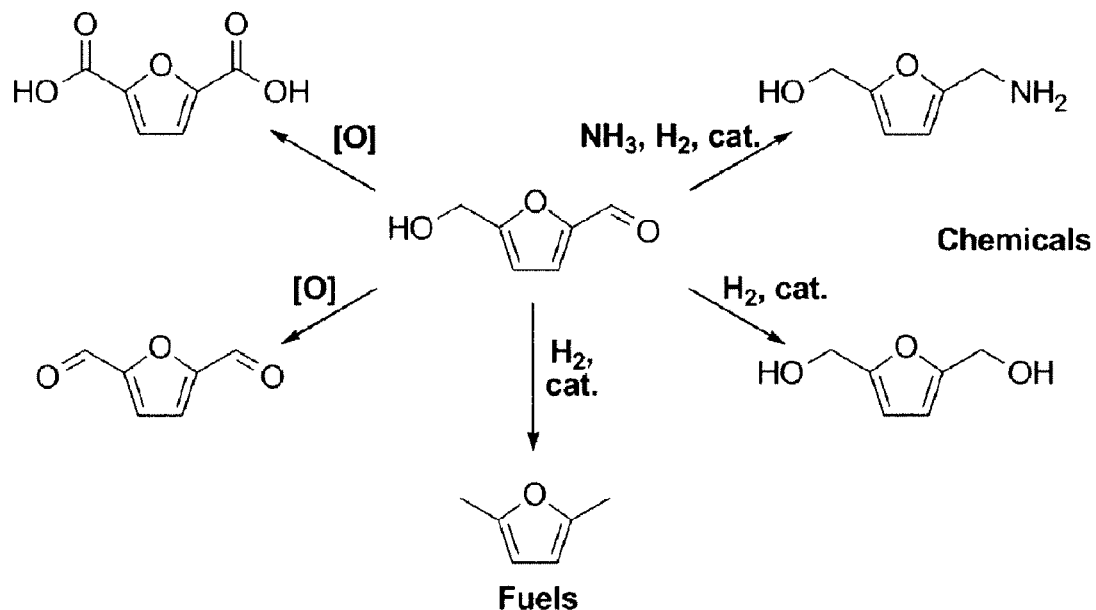
FIG. 1 illustrates that HMF can be converted by straightforward methods into a variety of useful acids, aldehydes, alcohols, and amines, as well as the promising fuel, 2,5-dimethylfuran (DMF).

The invention relates to chemical transformation of sugars and cellulosic biomass into fuels and chemicals. In general, any feedstock containing cellulose or sugars can be used in the methods of this invention, including cellulosic material and lignocellulosic material. The term cellulosic material (or biomass) is used generally herein to refer to any material containing cellulose.

The term "cellulose" is used broadly herein to refer to cellulose from any source and includes alpha-cellulose, beta-cellulose and gamma-cellulose and mixtures thereof. Cellulose can be characterized by its degree of polymerization (DP, average number of anhydroglucose units) which can range from tens of thousands to hundreds, e.g., 10,000-12,000 to 300. Cellulose as used herein also refers to underivatized cellulose or derivatives of cellulose, such as ethyl- or methylcellulose, hydroxyalkyl cellulose (e.g., hydroxypropyl cellulose), carboymethylcellulose, or mixtures thereof. In specific embodiments, the method of this invention is particularly useful for underivatized cellulose or cellulose derivatives which are water-insoluble. In specific embodiments, the method of this invention is particularly useful for cellulose derived without chemical modification from natural sources. Cellulose and cellulosic material may contain water.

Lignocellulosic material (or biomass) refers to any material that contains cellulose and lignin wherein the cellulose may be tightly bound to the lignin. Lignocellulosic material may also include hemicellulose or other polysaccharides such as xylan, arabinan or mannan. Lignocellulosic materials include among others wood residues, paper waste, plants, crops and agricultural residues (including among others, corn stover, poplar wood, switch grass, Miscanthus giganteus and sugarcane bagasse).

Lignocellulose or lignocellulosic material may be pretreated by physical methods (grinding, chopping or mashing) or by chemical or biological (e.g., enzymatic) methods as are known in the art which may increase the accessibility of cellulose or other biomass polysaccharide to hydrolysis. Such chemical or biological pre-treatments are however, not required for the practice of this invention. Lignocellulose and lignocellulosic material may contain water.

The term sugars is also used generally herein to refer to any saccharides (mono-, di-, trisaccharides etc.) and polysaccharides. The term carbohydrate is used broadly herein to refer to any material, feedstock or biomass that contains sugars, saccharides, or polysaccharides, including without limitation, cellulose, hemicellulose and lignocellulosic material. A "carbohydrate comprising a 6-carbon sugar" refers to any material, feedstock or biomass which contains a 6-carbon sugar molecule, a 6-carbon sugar attached to another chemical species or where a 6-carbon sugar is a monomer in an oligomer or polymer therein. A "carbohydrate comprising a 5-carbon sugar" refers to any material, feedstock or biomass which contains a 5-carbon sugar molecule, a 5-carbon sugar attached to another chemical species or where a 5-carbon sugar is a monomer in an oligomer or polymer therein.

The term "a furan" refers generally to furan and derivatives thereof, specifically including 5-hydroxymethylfurfural (HMF) and furfural. The term "furan" refers specifically to the molecule furan ($C_4H_4O$):

The reactions described herein for conversion of carbohydrates are carried out under reaction conditions (feedstock concentrations, reagent and catalyst concentrations, temperature, pressure and reaction time) effective for producing the desired furan product. One of ordinary skill in the art in view of the teachings herein and what is generally known in the art can select reaction conditions for carbohydrate conversion to achieve production of the desired furan.

The terms "polar aprotic solvent," "ionic liquid" and other chemical terminology as used herein is intended to have its broadest art-recognized meaning that is not inconsistent with the disclosure herein. Polar aprotic solvents, certain ionic liquids and certain miscible mixtures thereof can be employed as solvents herein for carbohydrates and biomass and for the conversion of such materials to one or more furans. Lignocelluosic materials need not be soluble in these solvents. Such materials may be decrystallized, swollen, partially solubilized or structurally disrupted by contact with the solvents herein.

The term polar aprotic solvent is used to refer to solvents which have a dielectric constant of greater than about 15, a sizeable permanent dipole moment and that cannot donate suitably labile hydrogen atoms to form strong hydrogen bonds. [See: "GLOSSARY OF TERMS USED IN PHYSICAL ORGANIC CHEMISTRY", IUPAC Recommendations 1994, P. Müller, Pure Appl. Chem., 66, 1077-1184 (1994)]. Polar aprotic solvents are also called dipolar aprotic solvents. Polar aprotic solvents include among others N,N-dialkylacetamides, N,N-dialkylformamides, 2-pyrrolidones or 3-pyrrolidones (including alkyl- or N-alkyl-substituted pyrrolidinones), pyrolidine carboxaldehydes, dialkylsulfones, including cyclic sulfolanes, including alkyl or dialkyl sulfolanes, dialkyl sulfoxides, an alkyl or N-alkyl substituted lactam, or a dialkyl propionamide, wherein alkyl groups are preferably those having 1-6 carbon atoms or those having 1-3 carbon atoms and wherein the alkyl groups may be straight-chain, branched or cyclic. Useful solvents include among others, N,N-dimethylacetamide (DMA), N,N-diethylacetamide (DEA), dimethylformamide (DMF), N-methylpyrrolidone, 1-ethyl-2-pyrrolidinone, methylsulfonylmethane, sulfolane, 3-methylsulfolane, 2,4-dimethylsulfolane, dimethylsulfoxide, diethylsulfoxide, N-methylcaprolactam, N,N-dimethylpropionamide, 1-pyrolidine carboxaldehyde; or miscible mixtures thereof. Preferred solvents include DMA and N-methylpyrrolidone. Additional polar aprotic solvents include acetone, and other ketones, nitroalkanes, such as nitromethane and nitroethane, hexamethylphosphoramide, and hexamethylphosphorous triamide. Acetone and other ketones are less preferred for use in this reaction because of potential formation of ketals (from ketones) with sugar hydroxyl groups. Nitroalkanes are less preferred for use in this reaction because of potential side reactions with saccharides or furan products.

1,4-Dioxane and n-butanol are not polar aprotic solvents, but as shown in Table 4, they can be used for conversion of glucose to HMF at relatively low yields. Acetonitrile and pyridine are not useful for conversion of glucose to HMF.

An ionic liquid is a salt that melts near or below ambient room temperature. For use in the methods herein the ionic liquid is liquid at the reaction temperature. The ionic liquid is one in which cellulose is soluble to some measurable extent. Preferably the ionic liquid is one in which up to about 5-25 weight % or more cellulose is soluble. More preferably the ionic liquid is one in which up to about 25 weight % or more cellulose is soluble. A number of ionic liquids have been shown in the art to dissolve cellulose. In specific embodiments, the cation of the ionic liquid is an organic cation, particularly a cation containing at least one positively charged nitrogen atom. In specific embodiments, the ionic liquid is an alkylimidazolium ionic liquid, more particularly an alkylimidazolium chloride ionic liquid. In additional specific embodiments, the ionic liquid is a 1,3-dialkyl-imidazolium chloride or a 1,2,3-trialkylimidazolium chloride. In more specific embodiments, the ionic liquid is [EMIM]Cl (1-ethyl-3-methylimidazolium chloride), [BMIM]Cl (1-butyl-3-methyl-imidazolium chloride), or 1-ethyl-2,3-dimethylimidazolium chloride, or a mixture thereof. In specific embodiments, the ionic liquid is an alkylpyridinium ionic liquid, more particularly an alkylpyridinium chloride ionic liquid. In additional specific embodiments, the ionic liquid is a 1-alkylpyridinium ionic liquid or a 1,4-dialkylpyridinium chloride. In more specific embodiments, the ionic liquid is 1-ethylpyridinium chloride, 1-butyl-4-methylpyridinium chloride, or a mixture thereof. Additional ionic liquids useful in the invention particularly those in which chloride is the anion of the salt of the ionic liquid, are provided in US 2008/0033187. Additional organic cations of ionic liquids are described in US 2009/0062524, WO2009030950, WO2009030849, US20090020112, WO2008112291, US20080227162 and WO2009024607, each of which is incorporated by reference herein for descriptions of such cations.

Ionic liquids may be characterized by either the anion or cation of the salt. For example, the term "chloride-containing ionic liquid" refers to an ionic liquid in which the anion of the salt is chloride analogous terms may be used for ionic liquids containing other anions, such as "bromide-containing ionic liquid" or "trifluoracetate-containing ionic liquid." With respect to characterization by cation, the term "alkylimidazolium-containing ionic liquid" and similar terms reciting the cations of ionic liquids refers to an ionic liquid wherein the cation has the structure named.

The term "complexing agent" is used herein to refer to a chemical species, typically an organic compound, which strongly binds certain cations, forming complexes. It will be appreciated by those of ordinary skill in the art that a given complexing agent may exhibit enhanced ability to complex a given cation or cations. One of ordinary skill in the art in view of information that is well known in the art can select a complexing agent that is appropriate for complexing a given cation. Crown ethers, aza-crowns, mixed aza crown ethers, cryptands, podands, and calixarenes are examples of complexing agents which can be employed in the methods herein to complex one or more cations of the chloride, bromide or iodide salts employed in the methods of this invention. 12-crown-4,15-crown-5,18-crown-6 and dibenzo-18-crown 6 are examples of crown ethers useful in this invention. For example, 12-crown-4 is particularly useful for complexing $Li^+$, 15-crown-5 is particularly useful for complexing $Na^+$, and 18-crown-6 is particularly useful for complexing $K^+$. Cyclen, cylam and 4,13-diaza-18-crown-6 are additional examples of complexing agents useful in the methods herein. [2.2.2]Cryptand is an example of a cryptand useful in the methods herein. In specific embodiments, the chloride, bromide and iodide salts are alkali metal or alkaline earth metal salts. In more specific embodiments, the chloride, bromide and iodide salts are $Li^+$, $Na^+$, $K^+$ or $Cs^+$ salts. Without wishing to be bound by any particular theory, it is believed that addition of the complexing agent in addition to the chloride, bromide or iodide salt(s), functions to complex the cation of the salt(s) to reducing its ion pairing with chloride, bromide or iodide, making the halide anion a more effective catalyst.

In specific embodiments, the amount of complexing agent added is that amount that enhances solubilization or dissolution of the carbohydrate or that enhances production of the furan product. In general, the amount employed ranges from about 20% lower than equimolar to 20% higher than equimolar compared to the total molar amount of cation of the chloride, bromide and/or iodide salt added to the solvent. More specifically, the amount of complexing agent employed ranges from 10% lower than equimolar to 10% higher than equimolar compared to the total molar amount of cation in the added salt. Yet more specifically, the amount of complexing agent employed is about equimolar to the total molar amount of cation in the added salt.

Figure 2:
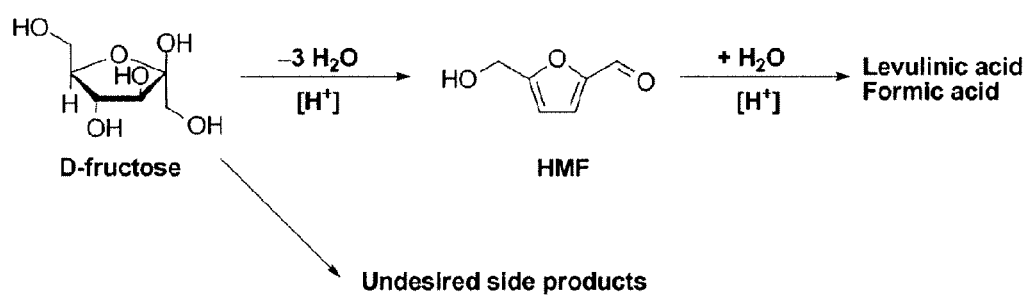
FIG. 2 illustrates dehydration of fructose to make HMF and schematically illustrates the potential for formation of undesired side-products and that HMF itself can be further dehydrated.
Figure 3:
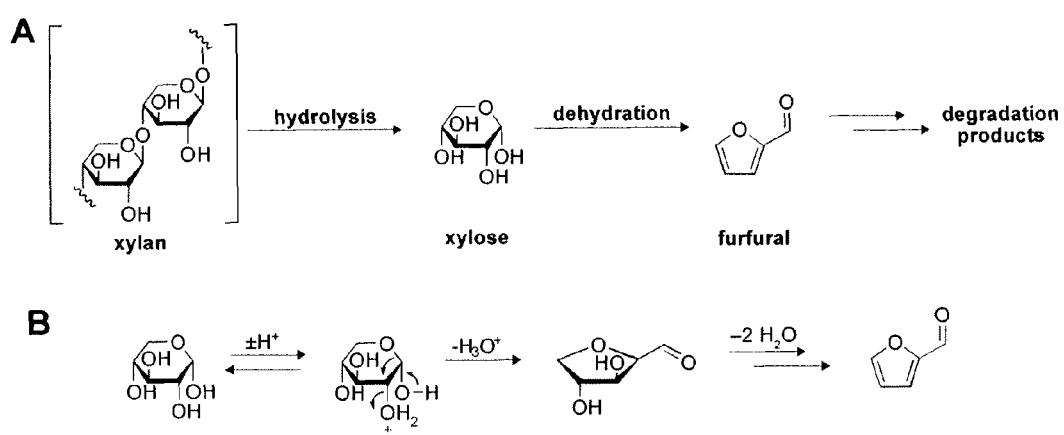
FIG. 3 illustrates proposed mecahnisms for synthesis of furfural. (A) Illustrates that furfural may be produced from xylan by hydrolysis into xylose and subsequent dehydration. (B) Illustrates the most likely mechanism for acid-catalyzed dehydration of xylose, in which displacement of the C-2 hydroxyl group leads to a 2,5-anhydride intermediate which readily loses water to form furfural.
Figure 5A:
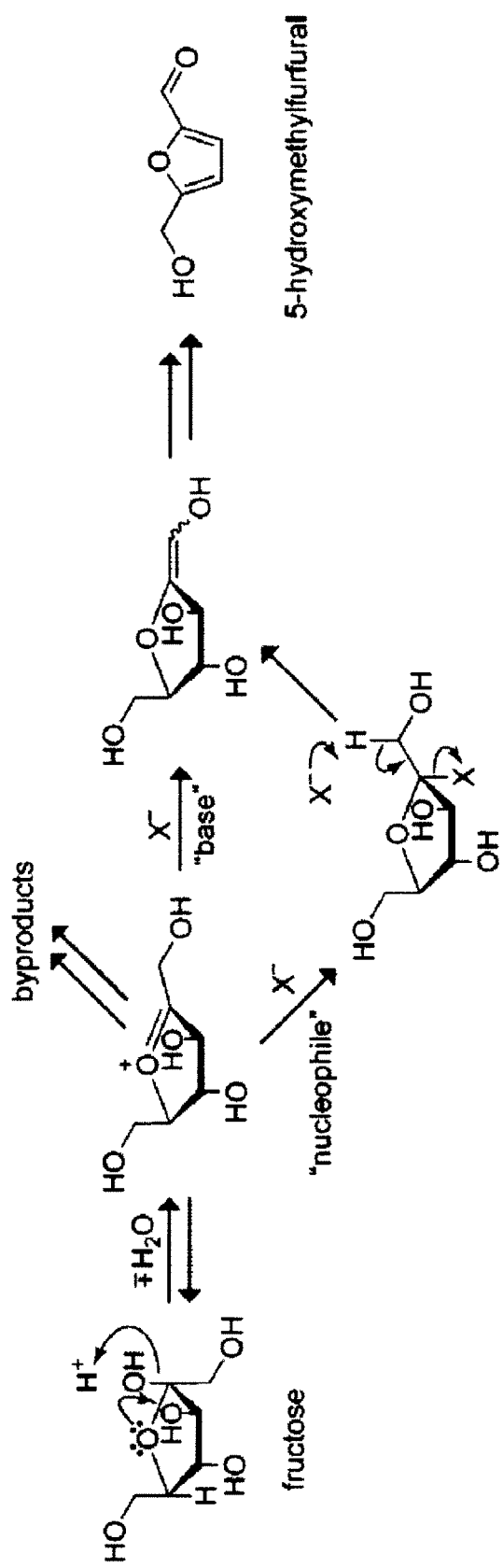
FIGS. 5A and 5B illustrate proposed mechanisms for certain reactions of this invention.
Figure 5B:
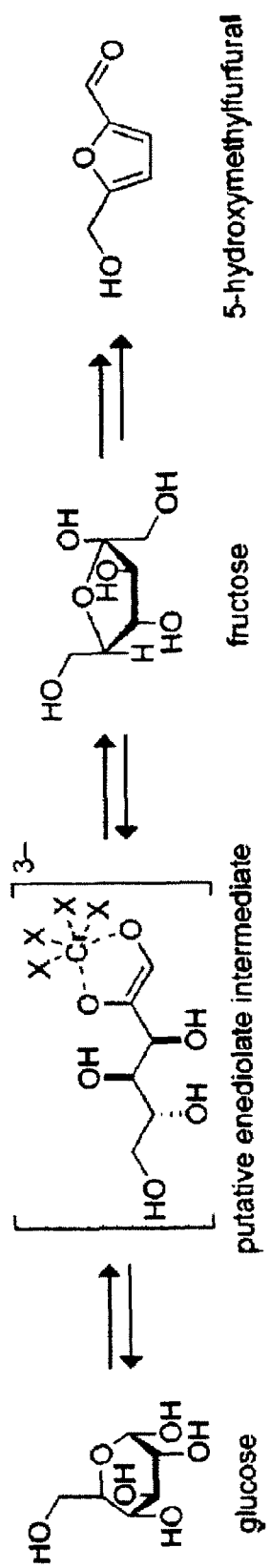
Figure 6:
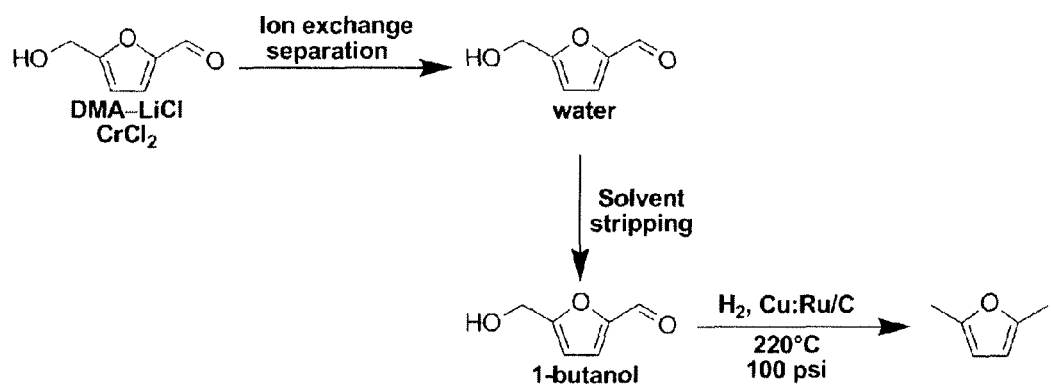
FIG. 6 illustrates an exemplary scheme for conversion of HMF to DMF. In this scheme, HMF is prepared by conversion of a carbohydrate by a process of this invention, and the reaction product is first purified by ion exchange separation to remove halide salt, followed by removal of the eluting solvent by solvent stripping, and the HMF is then converted by hydrogenolysis to DMF.

The invention also provides a method for making HMF derivatives which are useful fuels or chemicals, particularly DMF, which comprises, as a first step, making HMF by a method of this invention from a carbohydrate or carbohydrate feedstock and thereafter converting HMF to other useful fuels or chemicals, particularly DMF. HMF can be converted to carious useful chemicals by art-known methods as illustrated in FIGS. 1-3. For example, HMF is converted to DMF via hydrogenolysis. Hydrogenolysis can be conducted, for example, employing a copper catalyst and particularly using a copper-ruthenium catalyst or a copper chromite catalyst. Specific useful catalysts include $Cu/Cr_2O_3$ with optional promoters including Ba and Cu:Ru/carbon catalysts. Exemplary catalysts are provided in the following references: [Adkins, "Reactions of Hydrogen with Organic Compounds over Copper-Chromium Oxide and Nickel Catalysts;" University of Wisconsin Press: Madison, Wis. (1937); Roman-Leshkov et al., Nature 447, 982-986 (2007)]. A specific exemplary scheme for conversion of HMF to DMF is illustrated in FIG. 5 herein. In this scheme, HMF is prepared by conversion of a carbohydrate as described herein, and the reaction product is first purified by ion exchange separation to remove halide salt, followed by removal of the eluting solvent, e.g., water, e.g., by solvent stripping, and the HMF is then converted by hydrogenolysis to DMF.

The invention also provides a method for making furan which comprises, as a first step, making furfural by a method of this invention from a carbohydrate or carbohydrate feedstock comprising 5-carbon sugars and thereafter converting furfural to furan. Furfural made by the methods herein can be converted to other useful fuels by methods that are known in the art. In a specific embodiment, furfural is converted to furan via decarbonylation by methods that are known in the art. In a specific embodiment, decarbonylation of furfural is catalyzed by a catalyst selected from lime; a mixture of zinc chromite and manganese chromite; metal catalysts, in particular palladium, rhodium, ruthenium, platinum and nickel; a catalyst containing noble metals or a zeolite. Decarbonylation methods as described, for example, in U.S. Pat. Nos. 2,223,714; 3,257,417; 3,007,941; 4,764,627; or 4,780,552. In a more specific embodiment, furan can be decarbonylated in the presence of hydrogen and a catalyst which contains platinum and/or rhodium and cesium. In another more specific embodiment, furfural can be decarbonylated by passing furfural vapors over zeolites.

This invention provides a low-temperature (<250° C.), nonenzymic route from lignocellulosic biomass to fuels. Most other chemical methods for the conversion of lignocellulosic biomass to fuels use extreme temperatures to produce pyrolysis oil or synthesis gas, incurring substantial energy costs. This low temperature chemical conversion also has inherent advantages over bioprocessing for cellulosic fuels and chemicals. Fermentation of lignocellulosic feedstocks requires saccharification through extensive pretreatment, fragile enzymes, and engineered organisms. In contrast, our chemical process uses simple, inexpensive catalysts to transform cellulose into a valuable product in an ample yield. In addition, our privileged solvents enable rapid biomass conversion at useful solid loadings (10 wt %). the present method can, for example, transform 42% of the dry weight of cellulose into HMF and 19% of the dry weight of corn stover into HMF and furfural in one step. For comparison, cellulosic ethanol technology, which has been optimized extensively, enables the conversion of 24% of the dry weight of corn stover into ethanol in a complex process involving multiple chemical, biochemical, and microbiological steps. [Aden, A. Biochemical Production of Ethanol from Corn Stover: 2007 State of Technology Model; Report NREL/TP-510-43205; National Renewable Energy Laboratory, Golden, Colo., 2008; http://www.nrel.gov/docs/fy08osti/43205.pdf.] The 2-step process of this invention is also competitive on the basis of energy yield. The HMF and furfural products contain 43% of the combustion energy available from cellulose and xylan in the corn stover starting material, whereas ethanol from corn stover preserves 62% of the sugar combustion energy.

Biomass components that cannot be converted into HMF, such as lignin, can be reformed to produce $H_2$ for HMF hydrogenolysis (FIG. 3) or burned to provide process heat. [Navarro, R. M.; Pena, M. A.; Fierro, J. L. Chem. Rev. 2007, 107,3952-3991.]

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. Compounds described herein may exist in one or more isomeric forms, e.g., structural or optical isomers. When a compound is described herein such that a particular isomer, enantiomer or diastereomer of the compound is not specified, for example, in a formula or in a chemical name, that description is intended to include each isomers and enantiomer (e.g., cis/trans isomers, R/S enantiomers) of the compound described individual or in any combination. Specific names of compounds are intended to be exemplary, as it is known that one of ordinary skill in the art can name the same compounds differently.

Molecules disclosed herein may contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. The broad term comprising is intended to encompass the narrower consisting essentially of and the even narrower consisting of. Thus, in any recitation herein of a phrase "comprising one or more claim element" (e.g., "comprising A and B), the phrase is intended to encompass the narrower, for example, "consisting essentially of A and B" and "consisting of A and B." Thus, the broader word "comprising" is intended to provide specific support in each use herein for either "consisting essentially of" or "consisting of." The invention illustratively described herein suitably may be practiced in the absence of any element or elements, limitation or limitations which is not specifically disclosed herein.

One of ordinary skill in the art will appreciate that starting materials, carbohydrate feedstocks, catalysts, reagents, synthetic methods, purification methods, analytical methods, and assay methods, other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by examples, preferred embodiments and optional features, modification and variation of the concepts herein disclosed may be resorted to by those skilled in the art, and that such modifications and variations are considered to be within the scope of this invention as defined by the appended claims.

All references cited herein are hereby incorporated by reference to the extent that there is no inconsistency with the disclosure of this specification. Some references provided herein are incorporated by reference to provide details concerning sources of starting materials; alternative starting materials, reagents, methods of synthesis, purification methods, and methods of analysis; as well as additional uses of the invention.

THE EXAMPLES

General Experimental Procedures

Commercial chemicals were of reagent grade or better, and were used without further purification. With the exception of hydrogenolysis, reactions were performed in glass vessels heated in a temperature-controlled oil bath with magnetic stirring. The term "concentrated under high vacuum" refers to the removal of solvents and other volatile materials using a rotary evaporator at vacuum attained by a mechanical belt-drive oil pump while maintaining the water-bath temperature below 30° C. Conductivity was measured using an Extech Instruments ExStik II conductivity meter. 1-Ethyl-3-methylimidazolium chloride (99.5%, [EMIM]Cl) was obtained from Solvent-Innovation (Cologne, Germany). 1-Ethyl-3-methylimidazolium tetrafluoroborate (97%, [EMIM]$BF_4$) was obtained from Aldrich (Milwaukee, Wis.). 1-Ethyl-3-methylimidazolium triflate (98.5%, [EMIM]OTf), 1-butyl-3-methylpyridinium chloride (97%, [BMPy]Cl), 1-ethyl-3-methylimidazolium bromide (97%, [EMIM]Br), and 1-propyl-3-methylimidazolium iodide (97%, [PMIM]I) were obtained from Fluka (Geel, Belgium). 1-Ethylpyridinium chloride (98%, [EtPy]Cl) and 1-ethyl-2,3-dimethylimidazolium chloride (98%, [MMEIM]Cl) were obtained from Acros (Buchs, Switzerland). Cu:Ru/carbon catalyst (3:2 mole ratio Cu:Ru) was prepared by the method of Dumesic et al. using 5% Ru/carbon from Aldrich (Milwaukee, Wis.).[Roman-Leshkov et al., Nature 447, 982-986 (2007)] Cellulose (medium cotton linters) and xylan (from birchwood; >98% xylose following hydrolysis) were obtained from Sigma (St. Louis, Mo.). Milled and sieved corn stover and AFEX-treated corn stover were generously provided by B. E. Dale and coworkers (Michigan State University).[Chundawat et al., Biotechnol. Bioeng. 96, 219-231 (2006)] Cellulose and corn stover were dried to constant weight at 120° C. prior to use.

All reaction products were analyzed by HPLC and quantified using calibration curves generated with commercially-available standards. Following a typical reaction, the product mixture was diluted with a known mass of deionized water, centrifuged to sediment insoluble products, and analyzed. HPLC was performed with either a Waters system equipped with two 515 pumps, a 717 Plus autosampler, and a 996 photodiode array detector or an Agilent 1200 system equipped with refractive index and photodiode array detectors. HMF and furfural were analyzed using either a reversed-phase Varian Microsorb-MV 100-5 250×4.6 mm C18 column (1 ml/min, 93:7 water:acetonitrile, 35° C.) or an ion-exclusion Aminex HPX-87H 300×7.8 mm column (0.9 ml/min, 5 mM $H_2SO_4$, 65° C.). DMF was analyzed using a reversed-phase Varian Microsorb-MV 100-5 250×4.6 mm C18 column (1 ml/min, 55:45 water:acetonitrile, 35° C.).

Example 1

Production of HMF from Fructose

Fructose (10 wt %), catalyst, salt and any other additives (as indicated) were mixed in DMA in a glass vial. The vial was capped and the reaction mixture was stirred at the indicated temperature. At intervals aliquots of the reaction mixture were removed for HPLC analysis. The results are summarized in Table 1.

TABLE 1

Production of HMF from Fructose[a]

| solvent | catalyst (mol %) | additives (wt %) | temp. (° C.) | time (h) | molar yield (%) |
|---|---|---|---|---|---|
| DMA-LiCl (10%) | — | — | 80 | 5 | 58 |
| DMA-LiCl (10%) | — | — | 100 | 4 | 62 |
| DMA-LiCl (10%) | — | — | 120 | 2 | 65 |
| DMA-LiCl (10%) | — | — | 140 | 0.5 | 55 |
| DMA-LiCl (10%) | $H_2SO_4$, 6 | — | 80 | 4 | 66 |
| DMA-LiCl (10%) | $CuCl_2$, 6 | — | 80 | 4 | 66 |
| DMA-LiCl (10%) | $RuCl_3$, 6 | — | 80 | 4 | 58 |
| DMA-LiCl (10%) | $PdCl_2$, 6 | — | 80 | 5 | 60 |
| DMA-LiCl (10%) | CuCl, 6 | — | 80 | 5 | 62 |
| DMA-LiCl (1%) | $H_2SO_4$, 6 | — | 80 | 1 | 57 |
| DMA | $H_2SO_4$, 6 | — | 80 | 1 | 16 |
| DMA-LiCl (10%) | $H_2SO_4$, 6 | — | 100 | 5 | 63 |
| DMA-LiCl (10%) | $CuCl_2$, 6 | — | 100 | 4 | 55 |
| DMA-LiCl (10%) | $RuCl_3$, 6 | — | 100 | 5 | 65 |
| DMA-LiCl (10%) | $PdCl_2$, 6 | — | 100 | 4 | 62 |
| DMA-LiCl (10%) | CuCl, 6 | — | 100 | 5 | 62 |
| DMA-LiCl (10%) | $CrCl_2$, 6 | — | 100 | 5 | 66 |
| DMA-LiCl (10%) | $H_2SO_4$, 6 | — | 120 | 1 | 68 |
| DMA-LiCl (0.5%) | $H_2SO_4$, 6 | — | 120 | 0.2 | 81 |
| DMA-LiCl (10%) | CuCl, 6 | — | 120 | 3 | 71 |
| DMA-LiCl (10%) | $RuCl_3$, 6 | — | 120 | 1.5 | 61 |
| DMA-LiCl (10%) | $PtCl_2$, 6 | — | 120 | 3 | 66 |
| DMA-LiCl (10%) | $CuCl_2$, 6 | — | 120 | 3 | 65 |
| DMA-LiCl (10%) | $H_2SO_4$, 6 | — | 140 | 0.5 | 66 |
| DMA-LiCl (10%) | CuCl, 6 | — | 140 | 0.5 | 58 |
| DMA-LiCl (10%) | $PtCl_2$, 6 | — | 140 | 0.5 | 58 |
| DMA-LiCl (10%) | $CuCl_2$, 6 | — | 140 | 0.5 | 62 |
| DMA-LiCl (10%) | $CuCl_2$, 6 | [EMIM]Cl, 5 | 80 | 5 | 74 |
| DMA-LiCl (10%) | $CuCl_2$, 6 | [EMIM]Cl, 10 | 80 | 5 | 64 |
| DMA-LiCl (10%) | $CuCl_2$, 6 | [EMIM]Cl, 20 | 80 | 5 | 74 |
| DMA-LiCl (10%) | $CuCl_2$, 6 | [EMIM]Cl, 40 | 80 | 5 | 78 |
| DMA-LiCl (10%) | $H_2SO_4$, 6 | [EMIM]Cl, 5 | 80 | 4 | 70 |
| DMA-LiCl (10%) | $H_2SO_4$, 6 | [EMIM]Cl, 10 | 80 | 4 | 72 |
| DMA-LiCl (10%) | $H_2SO_4$, 6 | [EMIM]Cl, 20 | 80 | 4 | 78 |
| DMA-LiCl (10%) | $H_2SO_4$, 6 | [EMIM]Cl, 40 | 80 | 4 | 75 |
| DMA-LiCl (10%) | $CuCl_2$, 6 | [EMIM]Cl, 5 | 120 | 1 | 62 |
| DMA-LiCl (10%) | $CuCl_2$, 6 | [EMIM]Cl, 10 | 120 | 1.5 | 68 |
| DMA-LiCl (10%) | $CuCl_2$, 6 | [EMIM]Cl, 20 | 120 | 1 | 64 |
| DMA-LiCl (10%) | $CuCl_2$, 6 | [EMIM]Cl, 40 | 120 | 1 | 67 |
| DMA-LiCl (10%) | $H_2SO_4$, 6 | [EMIM]Cl, 5 | 120 | 1 | 61 |
| DMA-LiCl (10%) | $H_2SO_4$, 6 | [EMIM]Cl, 10 | 120 | 1 | 67 |
| DMA-LiCl (10%) | $H_2SO_4$, 6 | [EMIM]Cl, 20 | 120 | 1 | 69 |
| DMA-LiCl (10%) | $H_2SO_4$, 6 | [EMIM]Cl, 40 | 120 | 1 | 75 |
| DMA-LiCl (10%) | CuCl, 6 | [EMIM]Cl, 5 | 120 | 1.5 | 62 |
| DMA-LiCl (10%) | CuCl, 6 | [EMIM]Cl, 10 | 120 | 1.5 | 70 |
| DMA-LiCl (10%) | CuCl, 6 | [EMIM]Cl, 20 | 120 | 1 | 67 |
| DMA-LiCl (10%) | CuCl, 6 | [EMIM]Cl, 40 | 120 | 1.5 | 83 |
| DMA-LiF (10%) | $H_2SO_4$, 6 | LiF, 10 | 80 | 2 | 0 |
| DMA | $CuCl_2$, 6 | LiF, 10 | 80 | 2 | 0 |
| DMA | $H_2SO_4$, 6 | NaCl, 10 | 80 | 1 | 71 |
| DMA | $H_2SO_4$, 6 | NaCl, 10 | 80 | 1 | 80 |
| DMA | $H_2SO_4$, 6 | CsF, 10 | 80 | 2 | 0 |
| DMA | $CuCl_2$, 6 | CsF, 10 | 80 | 2 | 0 |
| DMA | $H_2SO_4$, 6 | KCl, 1.5; 18-crown-6, 5.6 | 80 | 2 | 63 |
| DMA | $H_2SO_4$, 6 | KCl, 1.5 | 80 | 2 | 56 |
| DMA | $H_2SO_4$, 6 | KCl, 10 | 100 | 5 | 92 |
| DMA | $H_2SO_4$, 6 | NaI, 10 | 100 | 5 | 91 |
| DMA | $H_2SO_4$, 6 | NaI, 8 | 120 | 0.2 | 93 |
| DMA | $H_2SO_4$, 6 | NaI, 0.5 | 120 | 0.2 | 57 |
| DMA | $H_2SO_4$, 6 | LiI, 8 | 120 | 0.2 | 94 |
| DMA | $H_2SO_4$, 6 | LiI, 0.5 | 120 | 0.2 | 68 |
| DMA | $H_2SO_4$, 6 | LiBr, 10 | 120 | 0.25 | 85 |
| DMA-LiCl (10%) | $H_2SO_4$, 6 | [EMIM]$BF_4$, 20 | 100 | 2 | 71 |
| DMA | $H_2SO_4$, 6 | [EMIM]$BF_4$, 20 | 100 | 4 | 59 |
| DMA-LiCl (10%) | $H_2SO_4$, 6 | [EMIM]OTf, 20 | 100 | 1 | 71 |
| DMA | $H_2SO_4$, 6 | [EMIM]OTf, 20 | 100 | 2 | 48 |
| DMA | $H_2SO_4$, 6 | [EMIM]Cl, 20 | 100 | 2 | 84 |
| DMA | $H_2SO_4$, 6 | [EMIM]Br, 20 | 100 | 1 | 94 |
| DMA | $H_2SO_4$, 6 | [PMIM]I, 20 | 100 | 2 | 81 |
| DMA | $H_2SO_4$, 6 | [EtPy]Cl, 20 | 100 | 2 | 81 |
| DMA | $H_2SO_4$, 6 | [MBPy]Cl, 20 | 100 | 2 | 78 |
| DMA | $H_2SO_4$, 6 | [MMEIM]Cl, 20 | 100 | 2 | 79 |

[a]Fructose was reacted at a concentration of 10 wt % relative to the total mass of the reaction mixture. The solvent composition is indicated by the weight percent of LiCl relative to DMA with additive concentrations relative to the total mass of the reaction mixture. Catalyst loading is relative to fructose. Yields are based on HPLC analysis.

The invention is based at least in part on the discovery that HMF can be produced in moderate to high yields from by heating fructose in DMA-LiCl, alone or with added catalysts. It was known that N,N-Dimethylacetamide (DMA) containing LiCl can dissolve purified cellulose without modifying its chemical structure and can do so to a concentration of up to 15 wt %, and also that DMA-LiCl can also dissolve simple sugars. [McCormick, C. L.; Callais, P. A.; Hutchinson, B. H., Jr. (1985) Macromolecules, 18, 2394-2401; Potthast, A.; Rosenau, T.; Buchner, R.; Roder, T.; Ebner, G.; Bruglachner, H.; Sixta, H.; Kosma, P. (2002) Cellulose, 9,41-53.] It is believed, however, that this work is the first demonstration of production of furans, such as HMF, in such a solvent system.

When mixed with DMA-LiCl and heated to sufficiently high temperatures (80-140° C.), fructose was converted to HMF in moderate yields (55-65%; Table 1, Example 1). Increased yields up to 71% were obtained through catalysis by Brønsted acids (e.g., $H_2SO_4$) and metal chlorides (e.g., CuCl, $CuCl_2$, and $PdCl_2$). These yields of HMF are moderate when compared to the yields of up to 85% achieved in solvents such as DMSO and [EMIM]Cl. [Halliday, G. A.; Young, R. J., Jr.; Grushin, V. V. (2003) Org. Lett., 5, 2003-2005; Zhao, H.; Holladay, J. E.; Brown, H.; Zhang, Z. C. (2007) Science, 316, 1597-1600.] Addition of increasing amounts of [EMIM]Cl to the DMA-LiCl medium (Table 1) improved yields. In general addition of ionic liquids improved yields. The influence of addition of other additives on fructose dehydration in DMA as catalyzed by $H_2SO_4$ (Table 1) was also investigated. The trifluoromethanesulfonate and tetrafluoroborate salts of EMIM delivered modest HMF yields, which were increased by the addition of LiCl. Adding chloride containing-ionic liquids with a variety of cationic counterions delivered HMF in yields around 80%. These results suggested that chloride ion mediated the advantage of [EMIM]Cl as an additive. Furthermore, the reaction appeared to proceed better with the loosely ion-paired chloride afforded by ionic liquids than with lithium chloride. We also observed that the potassium-complexing agent 18-crown-6 increased the yield of HMF in reactions utilizing potassium chloride. Without wishing to be bound by any particular theory, these results indicate that the presence of weakly ion-paired halide ions favor the reaction. [Weaver, W. M.; Hutchison, J. D. J. Am. Chem. Soc. 1964,86, 261-265.]

Distinct differences in the ability of halide ions to mediate the formation of HMF from fructose in DMA containing $H_2SO_4$ were found. Fluoride ions were found to be completely ineffective in the reactions examined. This is likely due to the low nucleophilicity and high basicity of fluoride. On the other hand, bromide and iodide ions, which tend to be less ion-paired than fluoride or chloride, enabled exceptionally high HMF yields in DMA. For example, adding 10 wt % lithium bromide or potassium iodide enabled the conversion of 92% of fructose to HMF in 4-5 h at 100° C. (Table 1). These reactions were highly selective, resulting in only low levels of the colored byproducts and insoluble polymeric products (i.e., humins) often formed concurrently with HMF. [Lewkowski, J. *ARKIVOC* 2001, 17-54.] Kinetic analyses indicate that the rate of HMF formation has a first-order dependence on halide concentration (data not shown).

The results provide mechanistic insights regarding the conversion of fructose into HMF. In most depictions of this process, a fructofuranosyl oxocarbenium ion forms first and then deprotonates spontaneously at C-1 to form an enol. [Antal, M. J., Jr.; Mok, W. S. L.; Richards, G. N. (1990) Carbohydr. Res., 199, 91-109.] To account for the dramatic influence of halide on yield and rate, two variations on this mechanism (FIG. 4A) are proposed. In one, a halide ion ($X^-$) attacks the oxocarbenium ion to form a 2-deoxy-2-halo intermediate that is less prone to side reactions as well as reversion to fructose. This intermediate then loses HX to form the enol (nucleophile pathway). Alternatively, a halide ion could form the enol merely by acting as a base that deprotonates C-1 (base pathway). The known reactivity of sugars as well as the observations of this example of fructose reactivity support the nucleophile pathway. The fructofuranosyl oxocarbenium ion is known to be attacked readily by alcohols, borohydrides, and even fluoride, so it is reasonable to expect its being attacked by chloride, bromide, and iodide. [Poncini, L.; Richards, G. N. (1980) Carbohydr. Res., 87, 209-217; Garegg, P. J.; Lindberg, B. (1988) Carbohydr. Res., 176, 145-148; Defaye, J.; Gadelle, A. (1985) Carbohydr. Res., 136, 53-65.] Bromide and iodide are better nucleophiles and leaving groups than chloride, and are also more effective as ionic additives. A mechanism that requires the halide ion to act only as a base would invert the order of halide reactivity.

Example 2

Production of HMF from Glucose

Glucose (10 wt %), catalyst, salt and any other additives (including ionic liquid) were mixed in DMA in a glass vial. The vial was capped and the reaction mixture was stirred at the indicated temperature. At intervals aliquots of the reaction mixture were removed for HPLC analysis. The results are summarized in Table 2.

TABLE 2

Production of HMF from Glucose[a]

| solvent | catalyst (mol %) | additives (wt %) | temp. (° C.) | time (h) | molar yield (%) |
|---|---|---|---|---|---|
| DMA-LiCl (10%) | — | — | 100 | 6 | <1 |
| DMA-LiCl (10%) | — | [EMIM]Cl, 20 | 100 | 6 | <1 |
| DMA | $CrCl_2$, 6 | — | 100 | 4 | 60 |
| DMA | $CrCl_2$, 6 | — | 120 | 3 | 47 |
| DMA | $CrCl_2$, 6 | [EMIM]Cl, 8 | 120 | 3 | 57 |
| DMA | $CrCl_2$, 6 | [EMIM]Cl, 5 | 100 | 6 | 64 |
| DMA | $CrCl_2$, 6 | [EMIM]Cl, 10 | 100 | 6 | 67 |
| DMA | $CrCl_2$, 6 | [EMIM]Cl, 20 | 100 | 6 | 67 |
| DMA-LiCl (10%) | $CrCl_2$, 6 | — | 100 | 5 | 60 |
| DMA-LiCl (10%) | $CrCl_2$, 6 | — | 120 | 3 | 53 |
| DMA-LiCl (10%) | $CrCl_2$, 6 | — | 120 | 2 | 55 |
| DMA-LiCl (10%) | $CrCl_2$, 6 | [EMIM]Cl, 5 | 100 | 6 | 58 |
| DMA-LiCl (10%) | $CrCl_2$, 6 | [EMIM]Cl, 10 | 100 | 6 | 61 |
| DMA-LiCl (10%) | $CrCl_2$, 6 | [EMIM]Cl, 20 | 100 | 6 | 62 |
| DMA | $CrCl_2$, 6 | [EMIM]Cl, 5 | 120 | 5 | 67 |
| DMA | $CrCl_2$, 6 | [EMIM]Cl, 10 | 120 | 3 | 62 |
| DMA | $CrCl_2$, 6 | [EMIM]Cl, 20 | 120 | 3 | 63 |
| DMA-LiCl (10%) | $CrCl_2$, 6 | [EMIM]Cl, 5 | 120 | 3 | 64 |
| DMA-LiCl (10%) | $CrCl_2$, 6 | [EMIM]Cl, 10 | 120 | 5 | 70 |
| DMA-LiCl (10%) | $CrCl_2$, 6 | [EMIM]Cl, 20 | 120 | 5 | 66 |
| DMA-LiCl (10%) | $CrCl_3$, 6 | — | 120 | 2 | 55 |
| DMA | $CrCl_3$, 6 | [EMIM]Cl, 5 | 100 | 6 | 59 |
| DMA | $CrCl_3$, 6 | [EMIM]Cl, 10 | 100 | 6 | 63 |
| DMA | $CrCl_3$, 6 | [EMIM]Cl, 20 | 100 | 6 | 67 |
| DMA-LiCl (10%) | $CrCl_3$, 6 | [EMIM]Cl, 5 | 100 | 6 | 57 |
| DMA-LiCl (10%) | $CrCl_3$, 6 | [EMIM]Cl, 10 | 100 | 6 | 69 |
| DMA-LiCl (10%) | $CrCl_3$, 6 | [EMIM]Cl, 20 | 100 | 3 | 65 |
| DMA | $CrCl_3$, 6 | [EMIM]Cl, 5 | 120 | 3 | 62 |
| DMA | $CrCl_3$, 6 | [EMIM]Cl, 10 | 120 | 4 | 60 |
| DMA | $CrCl_3$, 6 | [EMIM]Cl, 20 | 120 | 3 | 64 |
| DMA-LiCl (10%) | $CrCl_3$, 6 | [EMIM]Cl, 5 | 120 | 3 | 61 |
| DMA-LiCl (10%) | $CrCl_3$, 6 | [EMIM]Cl, 10 | 120 | 3 | 61 |
| DMA-LiCl (10%) | $CrCl_3$, 6 | [EMIM]Cl, 20 | 120 | 2 | 62 |
| DMA-LiCl (10%)[b] | $CrCl_2$, 6 | [EMIM]Cl, 20 | 100 | 6 | 62 |
| DMA-LiCl (10%) | $CrK(SO_4) \cdot 12 H_2O$, 6 | [EMIM]Cl, 20 | 100 | 6 | 1 |
| DMA-LiCl (10%) | $CrBr_3$, 6 | [EMIM]Cl, 20 | 100 | 6 | 58 |
| DMA-LiCl (10%) | $Cr(NO_3)_3$, 6 | [EMIM]Cl, 20 | 100 | 6 | 59 |
| DMA-LiCl (10%) | $CrCl_2$, 6 | [EMIM]OTf, 20 | 100 | 2 | 59 |
| DMA | $CrCl_2$, 6 | [EMIM]OTf, 20 | 100 | 4 | 54 |
| DMA | $CrCl_2$, 6 | [EMIM]Br, 20 | 100 | 2 | 78 |
| DMA | $CrCl_2$, 6 | [PMIM]I, 20 | 100 | 1 | 55 |
| DMA | $CrCl_2$, 6 | [EtPy]Cl, 20 | 100 | 1 | 64 |
| DMA | $CrCl_2$, 6 | [MBPy]Cl, 20 | 100 | 2 | 63 |
| DMA | $CrCl_2$, 6 | [MMEIM]Cl, 20 | 100 | 1 | 76 |
| DMA | $CrCl_2$, 6 | LiBr, 10 | 100 | 4 | 79 |
| DMA-LiCl (5%) | $CrCl_2$, 6 | LiBr, 5 | 100 | 4 | 56 |
| DMA | $CrCl_2$, 6 | LiI, 10 | 100 | 4 | 54 |
| DMA | $CrCl_3$, 6 | LiBr, 10 | 100 | 6 | 79 |
| DMA | $CrBr_3$, 6 | LiBr, 10 | 100 | 6 | 80 |
| DMA | $CrBr_3$, 2 | LiBr, 10 | 100 | 6 | 76 |
| DMA | $CrBr_3$, 1 | LiBr, 10 | 100 | 6 | 66 |
| DMA | $CrCl_2$, 6 | NaBr, 10 | 100 | 5 | 77 |
| DMA | $CrCl_3$, 6 | NaBr, 10 | 100 | 5 | 81 |
| DMA | $CrCl_2$, 6 | [EMIM]Br, 20 | 100 | 5 | 78 |
| DMA-LiCl (10%)[b] | $CrCl_2$, 6 | [EMIM]Br, 20 | 100 | 6 | 62 |
| DMA-LiCl (10%) | $CrCl_2$, 6 | TMEDA, 1 | 120 | 3 | 28 |
| DMA-LiCl (10%) | $CrCl_2$, 6 | pyridine, 1 | 120 | 3 | 43 |

[a]Glucose was reacted at a concentration of 10 wt % relative to the total mass of the reaction mixture. The solvent composition is indicated by the weight percent of LiCl relative to DMA with additive concentrations relative to the total mass of the reaction mixture. Catalyst loading is relative to glucose. Yields are based on HPLC analysis.
[b]In this case, glucose was 45% in water.

Addition of $CrCl_2$ and $CrCl_3$ to DMA enable the conversion of glucose into HMF in yields up to 69% (Table 2). Negligible HMF yields (<1%) were found from glucose in the absence of chromium salts. With the addition of CrCl$_2$ to DMA or DMA-LiCl, substantial yields of HMF (47-60%) were found, which were improved further by adding [EMIM]Cl to the reaction mixture. Supplementing the solvent with up to 20% [EMIM]Cl resulted in HMF yields up to 69%, comparable to those obtained in [EMIM]Cl alone. [Zhao, H.; Holladay, J. E.; Brown, H.; Zhang, Z. C. (2007) Science, 316, 1597-1600.] As with fructose, a marked halide effect was observed. Although addition of iodide salts to the chromium chloride reaction mixture did not greatly change the HMF yield, using 10 wt % lithium or sodium bromide increased the HMF yield to 79-81% after 5-6 h at 100° C. These yields of HMF from glucose exceed those reported previously, approach typical yields of HMF from fructose, and do not require ionic liquid solvents. Moreover, glucose syrups like those readily available from corn are also excellent feedstocks for HMF synthesis by the methods herein.

It has been reported that CrCl$_2$ was markedly less effective than CrCl$_3$. [Zhao, H.; Holladay, J. E.; Brown, H.; Zhang, Z. C. (2007) Science, 316, 1597-1600.] The present results, however, show that chromium in either oxidation state gave a similar yield. Without wishing to be bound by any particular mechanism of action, chromium likely enables conversion of glucose to HMF by catalyzing the isomerization of glucose into fructose (FIG. 4B). [Zhao, H.; Holladay, J. E.; Brown, H.; Zhang, Z. C. (2007) Science, 316, 1597-1600.] The fructose is then converted to HMF.

Example 3

Production of HMF from Glucose in Various Solvents

Exemplary procedure: Glucose (10 wt %), LiCl (10 wt %), and CrCl$_2$ (6 mol %) were mixed in the indicated solvent in a glass vial. The vial was capped and the reaction mixture was stirred at the indicated temperature. After 3.25 h the reaction mixture was analyzed by HPLC. Experiments were performed with the indicated solvent with LiCl (10 wt %) and catalyst for the listed time at the listed temperature. The average results for two trials are summarized in Table 3.

TABLE 3

Production of HMF from Glucose in Various Solvents

| solvent | catalyst (mol %) | additives (wt %) | temp. (° C.) | time (h) | molar yield[b] (%) |
|---|---|---|---|---|---|
| DMA | CrCl$_2$, 6 | — | 120 | 3.25 | 45 |
| N,N-dimethylformamide | CrCl$_2$, 6 | — | 120 | 3.25 | 36 |
| N-methylpyrrolidone | CrCl$_2$, 6 | — | 120 | 3.25 | 45 |
| sulfolane | CrCl$_2$, 6 | — | 120 | 3.25 | 35 |
| dimethylsulfoxide | CrCl$_2$, 6 | — | 120 | 3.25 | 46 |
| acetonitrile | CrCl$_2$, 6 | — | 120 | 3.25 | 0 |
| dioxane | CrCl$_2$, 6 | — | 120 | 3.25 | 13 |
| 1-butanol | CrCl$_2$, 6 | — | 120 | 3.25 | 4 |
| pyridine | CrCl$_2$, 6 | — | 120 | 3.25 | 0 |
| 1-ethyl-2-pyrrolidinone | CrCl$_2$, 6 | — | 120 | 3.25 | 32 |
| N-methylcaprolactam | CrCl$_2$, 6 | — | 120 | 3.25 | 38 |
| diethylacetamide | CrCl$_2$, 6 | — | 120 | 3.25 | 28 |
| 1-pyrrollidine carboxaldehyde | CrCl$_2$, 6 | — | 120 | 3.25 | 33 |
| N,N-dimethylpropionamide | CrCl$_2$, 6 | — | 120 | 3.25 | 29 |

[a]Glucose was reacted at a concentration of 10 wt % relative to the total mass of the reaction mixture. Catalyst loading is relative to glucose. Yields are based on HPLC analysis.
[b]Average of two trials.

Investigation of the generality of chromium-catalyzed HMF synthesis revealed that a wide range of polar aprotic solvents afforded HMF from glucose in yields higher than those commonly achieved (Table 3). [Chheda, J. N.; Roman-Leshkov, Y.; Dumesic, J. A. Green Chem. 2007, 9, 342-350.] On the other hand, some coordinating classes of solvents, such as amines and alcohols, inhibit or prevent formation of HMF, perhaps because of their interactions with the chromium salts. No HMF was formed upon reaction of glucose in pyridine, and adding several equivalents (based on chromium) of pyridine or N,N,N',N'-tetramethylethylenediamine markedly decreased HMF formation in DMA-LiCl (Table 2). The basicity of these amines might also disfavor HMF formation. The observations of Tables 2 and 3 suggest that the yield of HMF from glucose in reactions utilizing chromium correlates with metal coordination. Highly coordinating ligands such as amines decrease the yield of HMF. On the other hand, halide ligands enhance HMF yields, with bromide being the most effective. The data suggest that the halide additives must balance two roles in the conversion of glucose into HMF: serving as ligands for chromium and facilitating the selective conversion of fructose. Although iodide excels in the latter role, its large size or low electronegativity could compromise its ability as a ligand. In contrast, bromide potentially offers the optimal balance of nucleophilicity and coordinating ability, enabling unparalleled transformation of glucose into HMF.

Example 4

Production of HMF from Sucrose

Sucrose (10 wt %), catalyst, salt, ionic liquid (if indicated) and any other additives were mixed in DMA in a glass vial. The vial was capped and the reaction mixture was stirred at the indicated temperature. At intervals aliquots of the reaction mixture were removed for HPLC analysis. The results are summarized in Table 4.

TABLE 4

Production of HMF from Sucrose

| solvent | catalyst (mol %) | additives (wt %) | temp. (° C.) | time (h) | molar yield (%) |
|---|---|---|---|---|---|
| DMA-LiCl (10%) | CrCl$_2$, 6 | — | 120 | 2 | 56 |
| DMA-LiCl (10%) | CrCl$_3$, 6 | — | 120 | 2 | 52 |
| DMA-LiCl (10%) | CrCl$_2$, 6 | [EMIM]Cl, 3 | 120 | 2 | 61 |
| DMA-LiCl (10%) | CrCl$_3$, 6 | [EMIM]Cl, 3 | 120 | 2 | 69 |
| DMA | CrCl$_2$, 6 | LiBr, 10 | 100 | 6 | 79 |
| DMA | CrCl$_3$, 6 | LiBr, 10 | 100 | 3 | 79 |

Example 5

Synthesis of HMF from Various Sugars

Data for reactions of mannose (Table 5A), galactose (Table 5B), lactose (Table 5C), tagalose (Table 5D), and psicose and sorbose (Table 5E) are provided. Reactions were carried out generally as discussed in Examples 1-4 with the indicated solvents, additives, amounts of reactions components, temperatures and times.

Exemplary results for conversion of mannose into HMF are provided in Table 5A. Mannose was reacted at a concentration of 10 wt % relative to the total mass of the reaction mixture. Additive concentrations are relative to the total mass of the reaction mixture. Catalyst loading is relative to mannose. Yields are based on HPLC analysis.

TABLE 5A

Synthesis of HMF from Mannose

| solvent | catalyst (mol %) | additives (wt %) | temp. (° C.) | time (h) | molar yield (%) |
|---|---|---|---|---|---|
| DMA | | LiCl, 10 | 120 | 2 | 2 |
| [EMIM]Cl | | | 120 | 2 | 1 |
| DMA | $CrCl_2$, 6 | LiCl, 10 | 120 | 2 | 54 |
| DMA | $CrCl_3$, 6 | LiCl, 10 | 120 | 2 | 43 |
| DMA | $CrCl_2$, 6 | LiBr, 10 | 120 | 2 | 51 |
| DMA | $CrCl_3$, 6 | LiBr, 10 | 120 | 2 | 64 |
| [EMIM]Cl | $CrCl_2$, 6 | | 120 | 2 | 57 |
| [EMIM]Cl | $CrCl_3$, 6 | | 120 | 2 | 56 |
| DMA | $CrCl_2$, 6 | LiCl, 10 | 100 | 2 | 54 |
| DMA | $CrCl_3$, 6 | LiCl, 10 | 100 | 2 | 47 |
| DMA | $CrCl_2$, 6 | LiBr, 10 | 100 | 2 | 69 |
| DMA | $CrCl_3$, 6 | LiBr, 10 | 100 | 2 | 60 |
| [EMIM]Cl | $CrCl_2$, 6 | | 100 | 2 | 68 |
| [EMIM]Cl | $CrCl_3$, 6 | | 100 | 2 | 52 |

In the absence of chromium(II) or chromium(III), lithe HMF was formed and nearly all mannose was recovered unchanged at 100° C. On the other hand, the addition of catalytic chromium enabled HMF yields of 43-54% in DMA-LiCl at 100-120° C. Higher HMF yields were obtained in either DMA-LiBr or [EMIM]Cl, with a maximum yield of 69% achieved at 100° C. These trends are comparable to those with glucose, suggesting that these two epimeric aldoses form HMF through a similar mechanism. It is believed that similar to glucose, mannose complexes with a chromium ion and upon deprotonation forms fructose. The fructose intermediate is then dehydrated into HMF.

Exemplary data for the conversion of galactose to HMF are provided in Table 5B. Galactose was reacted at a concentration of 10 wt % relative to the total mass of the reaction mixture. Additive concentrations are relative to the total mass of the reaction mixture. Catalyst loading is relative to galactose. Yields are based on HPLC analysis. No HMF was produced from galactose in the absence of chromium salts. With $CrCl_2$ or $CrCl_3$ in DMA-LiCl at 120° C., HMF was produced in 10% yield, far lower than the yields observed with glucose and mannose. Adding $H_2SO_4$ as a co-catalyst resulted in lower yields, while use of [EMIM]Cl as the solvent in place of DMA did not greatly improve the results. On the other hand, switching to non-chloride salts in the solvent increased HMF yields. Substituting LiBr for LiCl raised the HMF yield to 18%, and using $CrBr_3$ without a halide additive allowed a yield of 33%. The yields obtained were significantly lower than those observed for other aldoses.

TABLE 5B

Synthesis of HMF from Galactose

| solvent | catalyst (mol %) | additives (wt %) | temp. (° C.) | time (h) | molar yield (%) |
|---|---|---|---|---|---|
| DMA | | LiCl, 10 | 120 | 2 | 1 |
| [EMIM]Cl | | | 120 | 2 | 1 |
| [EMIM]Cl | $H_2SO_4$, 6 | | 120 | 2 | 1 |
| DMA | $CrCl_2$, 6 | LiCl, 10 | 120 | 2 | 10 |
| DMA | $CrCl_3$, 6 | LiCl, 10 | 120 | 2 | 10 |
| DMA | $CrCl_2$, 6; $H_2SO_4$, 6 | LiCl, 10 | 120 | 2 | 9 |
| DMA | $CrCl_3$, 6; $H_2SO_4$, 6 | LiCl, 10 | 120 | 2 | 7 |
| [EMIM]Cl | $CrCl_2$, 6 | | 120 | 2 | 14 |
| [EMIM]Cl | $CrCl_3$, 6 | | 120 | 2 | 4 |
| DMA | $CrCl_2$, 6 | LiBr, 10 | 120 | 2 | 18 |
| DMA | $CrCl_3$, 6 | LiBr, 10 | 120 | 2 | 17 |
| DMA | $CrCl_2$, 6; $H_2SO_4$, 6 | LiBr, 10 | 120 | 2 | 9 |
| DMA | $CrCl_3$, 6; $H_2SO_4$, 6 | LiBr, 10 | 120 | 2 | 9 |
| DMA | $CrCl_2$, 6 | | 120 | 2 | 22 |
| DMSO | $CrCl_2$, 6 | | 120 | 2 | 22 |
| DMA | $CrBr_3$, 6 | | 120 | 3 | 33 |
| DMSO | $CrBr_3$, 6 | | 120 | 3 | 24 |
| DMA | $Cr(NO_3)_3$, 6 | | 120 | 3 | 9 |
| DMSO | $Cr(NO_3)_3$, 6 | | 120 | 3 | 5 |

Exemplary data for conversion of lactose to HMF are provided in Table 5C. Lactose was reacted at a concentration of 10 wt % relative to the total mass of the reaction mixture. Additive concentrations are relative to the total mass of the reaction mixture. Catalyst loading is relative to lactose. Yields are based on HPLC analysis. Use of chloride-containing solvents resulted in yields HMF of about 20% from lactose, which are far lower than achieved with most other sugars. Slightly higher yields were obtained in DMA alone (i.e., without LiCl or other salt) and DMA containing bromide salts such as $CrBr_3$ enabled the highest yields. HMF yields from lactose parallel roughly the average of the yields from glucose and galactose under the same conditions. The likely mechanism of HMF formation from lactose provides a rationale for these results. Lactose can be cleaved into glucose and galactose units through acid catalysis, and $H_2SO_4$ probably aids in this process. The resulting glucose is efficiently converted into HMF through chromium catalysis, with the galactose unit forming HMF less readily.

TABLE 5C

Synthesis of HMF from Lactose

| solvent | catalyst (mol %) | additives (wt %) | temp. (° C.) | time (h) | molar yield (%) |
|---|---|---|---|---|---|
| [EMIM]Cl | | | 120 | 2 | 3 |
| [EMIM]Cl | $H_2SO_4$, 6 | | 120 | 2 | 3 |
| DMA | $CrCl_2$, 6 | LiCl, 10 | 120 | 2 | 23 |
| DMA | $CrCl_3$, 6 | LiCl, 10 | 120 | 2 | 19 |
| DMA | $CrCl_2$, 6; $H_2SO_4$, 6 | LiCl, 10 | 120 | 2 | 19 |
| DMA | $CrCl_3$, 6; $H_2SO_4$, 6 | LiCl, 10 | 120 | 2 | 22 |
| [EMIM]Cl | $CrCl_2$, 6 | | 120 | 2 | 17 |
| [EMIM]Cl | $CrCl_2$, 6; $H_2SO_4$, 6 | | 120 | 2 | 21 |
| DMA | $CrCl_2$, 6 | | 120 | 3 | 23 |
| DMSO | $CrCl_2$, 6 | | 120 | 2 | 23 |
| DMA | $CrCl_2$, 6; $H_2SO_4$, 6 | | 120 | 3 | 26 |
| DMSO | $CrCl_2$, 6; $H_2SO_4$, 6 | | 120 | 3 | 11 |
| DMA | $CrCl_2$, 6 | LiBr, 10 | 120 | 2 | 27 |
| DMA | $CrCl_3$, 6 | LiBr, 10 | 120 | 2 | 29 |
| DMA | $CrCl2$, 6; $H_2SO_4$, 6 | LiBr, 10 | 120 | 2 | 39 |
| DMA | $CrCl3$, 6; $H_2SO_4$, 6 | LiBr, 10 | 120 | 2 | 35 |
| DMA | $Cr(NO_3)_3$, 6 | | 120 | 3 | 4 |
| DMSO | $Cr(NO_3)_3$, 6 | | 120 | 3 | 13 |
| DMA | $CrB_{r3}$ | | 120 | 3 | 41 |

Exemplary data for conversion of tagatose to HMF are provided in Table 5D. Representative Reaction: Tagatose (18.2 mg, 101 μmol) and LiCl (16 mg) were dissolved in DMA (200 mg), and the reaction mixture was stirred at 120° C. for 2 hours. After the reaction, the solution was diluted with $H_2O$ (300 mg) and analyzed by HPLC. Tagatose was reacted at a concentration of 10 wt % relative to the total mass of the reaction mixture. Additive concentrations are relative to the total mass of the reaction mixture. Catalyst loading is relative to tagatose. Yields are based on HPLC analysis. In chloride-containing solvents with chromium or $H_2SO_4$ catalysts, yields of HMF from tagatose were typically less than 20%. Just as was observed with galactose, the highest yields of HMF were achieved in the absence of chloride ions. Moreover, the maximal yield from tagatose was 61%, which is significantly lower than thethe 80-90% yields commonly achieved with fructose. The results suggest that transformation of tagatose into HMF is less efficient than conversion of fructose by the methods herein. It appears that tagatose is less likely to undergo dehydration to produce HMF and more likely to participate in deleterious side reactions. Without wishing to be bound by any particular mechanism, the difference in reactivity of fructose and tagatose herein may result from differences in their tautomeric composition. As noted above, Dehydration of ketoses into HMF probably proceeds through the equilibrium protonation and dehydration of furanose form of the sugar to form an oxocarbenium intermediate. Thus, increased concentrations of the furanose tautomer form would increase the rate of this reaction. Fructose exists primarily in furanose forms (e.g., 48% β-furanose, 20% α-furanose, and 27% β-pyranose in DMSO at 27° C.). In contrast, tagatose, preferentially forms pyranose tautomers in both water and organics (e.g., 76% α-pyranose, 17% β-pyranose, 4% α-furanose and 3% β-furanose in DMSO at 27° C.).

TABLE 5D

Synthesis of HMF from Tagatose

| solvent | catalyst (mol %) | additives (wt %) | temp. (° C.) | time (h) | molar yield (%) |
|---|---|---|---|---|---|
| DMA | | | 120 | 2 | 0 |
| DMA | | LiCl, 10 | 120 | 2 | 9 |
| [EMIM]Cl | | | 120 | 2 | 15 |
| DMA | $CrCl_2$, 6 | LiCl, 10 | 120 | 2 | 10 |
| DMA | $CrCl_3$, 6 | LiCl, 10 | 120 | 2 | 8 |
| DMA | $H_2SO_4$, 6 | LiCl, 10 | 120 | 2 | 7 |
| DMA | $CrCl_2$, 6; $H_2SO_4$, 6 | LiCl, 10 | 120 | 2 | 11 |
| [EMIM]Cl | $CrCl_2$, 6 | | 120 | 2 | 14 |
| [EMIM]Cl | $CrCl_3$, 6 | | 120 | 2 | 10 |
| [EMIM]Cl | $H_2SO_4$, 6 | | 120 | 2 | 12 |
| [EMIM]Cl | $CrCl_2$, 6; $H_2SO_4$, 6 | | 120 | 2 | 9 |
| DMSO | $CrCl_2$, 6 | LiCl, 10 | 120 | 2 | 20 |
| DMSO | $H_2SO_4$, 6 | LiCl, 10 | 120 | 2 | 13 |
| DMSO | | LiCl, 10 | 120 | 2 | 14 |
| DMA | $H_2SO_4$, 6 | | 120 | 2 | 45 |
| DMSO | | | 120 | 2 | 52 |
| DMSO | Dowex | | 120 | 2 | 55 |
| DMSO | $H_2SO_4$, 6 | | 120 | 2 | 61 |
| DMA | $CrCl_2$, 6 | | 120 | 2 | 21 |
| DMSO | $CrCl_2$, 6 | | 120 | 2 | 27 |
| DMA | $CrCl_2$, 6 | LiBr, 10 | 120 | 2 | 13 |
| DMA | $CrCl_3$, 6 | LiBr, 10 | 120 | 2 | 12 |
| DMA | $H_2SO_4$, 6 | LiBr, 10 | 120 | 3 | 26 |

Exemplary data for conversion of psicose and sorbose to HMF are provided in Table 5E. Psicose and sorbose were reacted at a concentration of 10 wt % relative to the total mass of the reaction mixture. Additive concentrations are relative to the total mass of the reaction mixture. Catalyst loading is relative to sugar. Yields are based on HPLC. Psicose is the C-3 epimer of fructose and exists as 50% furanose tautomers in DMSO (15% β-furanose, 35% α-furanose, 24% α-pyranose, and 26% β-pyranose at 27° C.),[31] while sorbose is a C-5 epimer which is primarily pyranose (93% α-pyranose and 7% α-furanose in DMSO at 25° C.). The yield of HMF from psicose with $H_2SO_4$ in DMSO was higher than that of either tagatose or sorbose and similar to those obtained with fructose, which is consistent with the relatively high furanose preference of psicose. Yields of HMF from psicose and sorbose were similar under other conditions. In DMA and in the presence of LiCl both sugars formed HMF in 30-45% yields. In particular, sorbose and psicose delivered significantly higher yields than tagatose in the presence of lithium chloride. These results suggest that the interplay of hexulose structure and reactivity is subtle.

TABLE 5E

Synthesis of HMF from Psicose and Sorbose

| sugar | solvent | catalyst (mol %) | additives (wt %) | temp. (° C.) | time (h) | molar yield (%) |
|---|---|---|---|---|---|---|
| psicose | DMA | | LiCl, 10 | 120 | 3 | 35 |
| psicose | DMA | $H_2SO_4$, 6 | LiCl, 10 | 120 | 3 | 33 |
| psicose | DMA | $H_2SO_4$, 6 | | 120 | 3 | 30 |
| psicose | DMSO | | LiCl, 10 | 120 | 3 | 39 |
| psicose | DMSO | $H_2SO_4$, 6 | LiCl, 10 | 120 | 3 | 37 |
| psicose | DMSO | $H_2SO_4$, 6 | | 120 | 3 | 82 |
| sorbose | DMA | | LiCl, 10 | 120 | 3 | 39 |
| sorbose | DMA | $H_2SO_4$, 6 | LiCl, 10 | 120 | 3 | 38 |
| sorbose | DMA | $H_2SO_4$, 6 | | 120 | 3 | 37 |
| sorbose | DMSO | | LiCl, 10 | 120 | 3 | 45 |
| sorbose | DMSO | $H_2SO_4$, 6 | LiCl, 10 | 120 | 3 | 37 |
| sorbose | DMSO | $H_2SO_4$, 6 | | 120 | 3 | 60 |

Example 6

Synthesis of Furfural from Xylose

Exemplary data for conversion of xylose into furfural is provided in Table 6. Xylose was reacted at a concentration of 10 wt % relative to the total mass of the reaction mixture. The solvent composition is indicated by the wt % of LiCl relative to DMA with additive concentrations relative to the total mass of the reaction mixture. Catalyst loading is relative to xylose. Yields are based on HPLC analysis.

In a representative experiment, xylose (25.5 mg, 170 μmol) was mixed with DMA (225 mg) and $CrCl_2$ (2.5 mg, 20 μmol), and the reaction mixture was stirred at 100° C. for 4 h. For reactions of xylose using [EMIM]Cl, chromium salts were mixed with a portion of the ionic liquid (25 mg) before addition to the reaction mixture.

TABLE 6

Synthesis of Furfural from Xylose

| solvent | catalyst (mol %) | additives (wt %) | temp (° C.) | time (h) | molar yield (%) |
|---|---|---|---|---|---|
| DMA | | | 100 | 2 | <5 |
| DMA | $CrCl_3$, 6 | | 100 | 2 | 37 |
| DMA | $CrCl_3$, 6 | | 100 | 4 | 38 |
| DMA | $CrCl_3$, 6 | | 100 | 6 | 37 |
| DMA | HCl, 3 | | 100 | 2 | 3 |
| DMA | HCl, 6 | | 100 | 2 | 1 |

TABLE 6-continued

Synthesis of Furfural from Xylose

| solvent | catalyst (mol %) | additives (wt %) | temp (° C.) | time (h) | molar yield (%) |
|---|---|---|---|---|---|
| DMA | HCl, 12 | | 100 | 2 | 6 |
| DMA | HCl, 24 | | 100 | 2 | |
| DMA | HCl, 3 | [EMIM]Cl, 5 | 100 | 2 | 1 |
| DMA | HCl, 6 | [EMIM]Cl, 5 | 100 | 2 | 2 |
| DMA | HCl, 12 | [EMIM]Cl, 5 | 100 | 2 | 3 |
| DMA | $CrCl_3$, 6 | [EMIM]Cl, 5 | 100 | 2 | 37 |
| DMA | $CrCl_3$, 6 | [EMIM]Cl, 5 | 100 | 4 | 37 |
| DMA | $CrCl_3$, 6 | [EMIM]Cl, 5 | 100 | 6 | 34 |
| DMA | $CrCl_3$, 6 | [EMIM]Cl, 10 | 100 | 2 | 37 |
| DMA | $CrCl_3$, 6 | [EMIM]Cl, 10 | 100 | 4 | 37 |
| DMA | $CrCl_3$, 6 | [EMIM]Cl, 10 | 100 | 6 | 38 |
| DMA | $CrCl_3$, 6 | [EMIM]Cl, 20 | 100 | 2 | 40 |
| DMA | $CrCl_2$, 6 | [EMIM]Cl, 5 | 100 | 2 | 45 |
| DMA | $CrCl_2$, 6 | [EMIM]Cl, 10 | 100 | 2 | 38 |
| DMA | $CrCl_2$, 6 | [EMIM]Cl, 20 | 100 | 2 | 41 |
| DMA-LiCl (10%) | $CrCl_3$, 6 | [EMIM]Cl, 5 | 100 | 2 | 40 |
| DMA-LiCl (10%) | $CrCl_3$, 6 | [EMIM]Cl, 10 | 100 | 2 | 30 |
| DMA-LiCl (10%) | $CrCl_3$, 6 | [EMIM]Cl, 20 | 100 | 2 | 37 |
| DMA-LiCl (10%) | $CrCl_2$, 6 | [EMIM]Cl, 5 | 100 | 2 | 24 |
| DMA-LiCl (10%) | $CrCl_2$, 6 | [EMIM]Cl, 10 | 100 | 2 | 33 |
| DMA-LiCl (10%) | $CrCl_2$, 6 | [EMIM]Cl, 20 | 100 | 2 | 36 |
| DMA | $CrCl_3$, 6 | LiBr, 10 | 100 | 4 | 47 |
| DMA | $CrBr_3$, 6 | LiBr, 10 | 100 | 4 | 50 |
| DMA | $CrCl_2$, 6 | NaBr, 10 | 100 | 4 | 54 |
| DMA | $CrCl_2$, 6 | [BMIM]Br, 20 | 100 | 4 | 55 |
| DMA | $CrCl_2$, 6 | LiBr, 10 | 100 | 4 | 56 |

Reaction products were analyzed by HPLC and quantified using calibration curves generated with commercially-available standards. Following a typical reaction, the product mixture was diluted with a known mass of deionized water, centrifuged to sediment insoluble products, and analyzed. The concentrations of products were calculated from HPLC-peak integrations and used to calculate molar yields. HPLC was performed with an Agilent 1200 system equipped with refractive index and photodiode array detectors. Furfural was analyzed by ion-exclusion chromatography using a Bio-Rad Aminex® HPX-87H column (300×7.8 mm; 5 mM $H_2SO_4$, 0.6 or 0.9 mL/min, 65° C.).

Only low yields of furfural and moderate conversions of xylose were observed in DMA both alone or with HCl. For instance, 12 mol % HCl in DMA accomplished 47% conversion of xylose and only 6% yield of furfural. Although Brønsted acids such as HCl are typically used to produce furfural, these reactions are commonly carried out at temperatures greater than 150° C. Under the milder reaction conditions used acids alone were less effective for rapid xylose conversion. In contrast, xylose was converted into furfural in 30-40% yield in DMA using $CrCl_2$ and $CrCl_3$. With these catalysts, we observed no consistent effect of 1-ethyl-3-methylimidazolium ([EMIM]) chloride or lithium chloride additives on the furfural yield. Bromide additives such as 1-butyl-3-methylimidazolium ([BMIM]) bromide and lithium bromide improved furfural yields up to 56%. Yields in these reactions may be reduced by reactions of furfural with itself and with xylose to form oligomeric species. The contrast between furfural yields using acid and chromium catalysts suggests that an alternative mechanism of xylose dehydration may occur in the presence of chromium salts.

To investigate the mechanism of xylose dehydration, the initial rates of furfural appearance in DMA-LiCl with $CrCl_2$ were examined (data not shown). These analyses revealed that the rate of furfural formation has a first-order dependence on xylose concentration and a half-order dependence on chromium (II) concentration. These results indicate that chromium is directly involved in the mechanism of conversion prior to the rate-determining step, perhaps in a complex fashion. There appeared, however, to be no correlation with lithium chloride concentration.

Based on these results and on the differences between chromium and HCl catalysts, chromium may effect the transformation of xylose into xylulose to achieve xylose dehydration at lower temperatures. This suggested mechanism is analogous to that of chromium-catalyzed conversion of glucose into HMF in which chromium catalyzes xylose isomerization through an enediolate intermediate. Acting as a Lewis acid, the chromium salt can convert the resulting xylulose into an oxocarbenium ion. Deprotonation of this species produces an enol, which is dehydrated (loss of 2 molecules of water) to form furfural. This mechanism is consistent with observations of carbohydrate reactivity herein.

Example 7

Production of HMF from Cellulose

Cellulose (4 wt %), LiCl, [EMIM]Cl, and DMA were mixed at 50° C. for 24 h. To this mixture were added concd HCl and catalyst in [EMIM]Cl, and the reaction mixture was stirred in a capped glass vial at the indicated temperature for the indicated time. At intervals aliquots of the reaction mixture were removed for HPLC analysis. The results are summarized in Table 7.

TABLE 7

Production of HMF from Cellulose[a]

| solvent | catalyst (mol %) | additives (wt %) | temp. (° C.) | time (h) | molar yield (%) |
|---|---|---|---|---|---|
| DMA-LiCl (10%) | — | [EMIM]Cl, 40 | 140 | 2 | 4 |
| DMA-LiCl (10%) | $CrCl_2$, 25; HCl 10 | — | 140 | 2 | 22 |
| DMA-LiCl (10%) | $CrCl_3$, 25; HCl 10 | — | 140 | 2 | 33 |
| DMA-LiCl (10%) | $CrCl_2$, 25 | — | 140 | 6 | 15 |
| DMA-LiCl (15%) | $CrCl_3$, 36 | — | 140 | 6 | 17 |
| DMA-LiCl (10%) | $CrCl_2$, 25 | [EMIM]Cl, 10 | 140 | 4 | 18 |
| DMA-LiCl (10%) | $CrCl_2$, 25 | [EMIM]Cl, 20 | 140 | 4 | 24 |
| DMA-LiCl (10%) | $CrCl_2$, 25 | [EMIM]Cl, 40 | 140 | 4 | 33 |
| DMA-LiCl (10%) | $CrCl_2$, 25; HCl, 6 | [EMIM]Cl, 10 | 140 | 4 | 21 |
| DMA-LiCl (10%) | $CrCl_2$, 25; HCl, 6 | [EMIM]Cl, 20 | 140 | 4 | 33 |
| DMA-LiCl (10%) | $CrCl_2$, 25; HCl, 6 | [EMIM]Cl, 40 | 140 | 1 | 43 |
| DMA-LiCl (10%) | $CrCl_2$, 25; HCl, 6 | [EMIM]Cl, 60 | 140 | 2 | 54 |
| DMA-LiCl (10%) | $CrCl_2$, 25; HCl, 6 | [EMIM]Cl, 80 | 140 | 2 | 47 |
| DMA-LiCl (10%) | $CrCl_3$, 25; HCl, 6 | [EMIM]Cl, 10 | 140 | 4 | 22 |
| DMA-LiCl (10%) | $CrCl_3$, 25; HCl, 6 | [EMIM]Cl, 20 | 140 | 4 | 30 |
| DMA-LiCl (10%) | $CrCl_3$, 25; HCl, 6 | [EMIM]Cl, 40 | 140 | 4 | 38 |
| [EMIM]Cl | $CrCl_2$, 25; HCl, 6 | — | 140 | 1 | 53 |
| DMA-LiCl (10%) | $CrCl_2$, 25; HCl 10 | LiI, 1 | 140 | 2 | 7 |
| DMA-LiCl (10%) | $CrCl_2$, 25; HCl 10 | LiBr, 1 | 140 | 2 | 9 |
| DMA-LiCl (5%) | $CrCl_2$, 25; HCl 10 | LiI, 5 | 140 | 2 | <1 |
| DMA-LiCl (5%) | $CrCl_2$, 25; HCl 10 | LiBr, 5 | 140 | 2 | 6 |
| DMA-LiCl (10%) | $CrCl_3$, 25; HCl 10 | LiI, 2 | 140 | 1 | 27 |

TABLE 7-continued

Production of HMF from Cellulose[a]

| solvent | catalyst (mol %) | additives (wt %) | temp. (° C.) | time (h) | molar yield (%) |
|---|---|---|---|---|---|
| DMA-LiCl (10%) | CrCl$_3$, 25; HCl 10 | LiBr, 1 | 140 | 2 | 34 |
| DMA-LiCl (10%) | CrCl$_3$, 25; HCl 10 | LiI, 5 | 140 | 1 | 23 |
| DMA-LiCl (10%) | CrCl$_3$, 25; HCl 10 | LiBR, 3 | 140 | 2 | 37 |

[a]Cellulose was reacted at a concentration of 4 wt % relative to the total mass of the reaction mixture. Solvent composition is indicated by weight percent of LiCl relative to DMA with additive concentrations relative to the total mass of the reaction mixture. Catalyst loading and molar yield are relative to moles of glucose monomers contained in the cellulose in the starting material. Yields are based on HPLC analysis.

HMF has been traditionally obtained from monosaccharides. Cellulosic biomass is, however, an especially promising source because of its inexpensive availability from non-food resources. Unfortunately, the typical aqueous acid hydrolysis methods for producing HMF from cellulose rely on high temperatures and pressures (250-400° C., 10 MPa) and result in yields of 30%. [Kono, T.; Matsuhisa, H.; Maehara, H.; Horie, H.; Matsuda, K. Jpn. Pat. Appl. 2005232116, 2005.] Dissolution of purified cellulose in a mixture of DMA-LiCl and [EMIM]Cl and addition of CrCl$_2$ or CrCl$_3$ produced HMF from cellulose in up to 54% yield within 2 h at 140° C. (Table 7). These yields compare well with reports of HMF synthesis from cellulose using aqueous acid and ionic liquids. [Kono, T.; Matsuhisa, H.; Maehara, H.; Horie, H.; Matsuda, K. Jpn. Pat. Appl. 2005232116, 2005; Zhao, H.; Holladay, J. E.; Zhang, Z. C. U.S. Pat. Appl. 20080033187,2008.] Neither lithium iodide nor lithium bromide alone produced high yields of HMF because these salts in DMA do not dissolve cellulose. [McCormick, C. L.; Callais, P. A.; Hutchinson, B. H., Jr. *Macromolecules* 1985, 18, 2394-2401.] Using lithium bromide along with DMA-LiCl did enable modest improvements in yield. Likewise, using hydrochloric acid as a cocatalyst boosted yields.

Recently, Mascal and Nikitin reported an alternative method for producing furanic products, chiefly 5-chloromethylfurfural (CMF), from purified cellulose. Heating a solution of highly purified cellulose in concentrated hydrochloric acid and lithium chloride and then extracting the products with 1, 2-dichloroethane yielded this chlorinated relative of HMF in 71% isolated yield. CMF can be converted subsequently to potential fuels like DMF and 5-ethoxymethylfurfural. Although this process avoids the use of chromium and results in higher yields (84% isolated yield of furanic products versus 54%), it has notable drawbacks relative to the methods of this invention. [Mascal, M.; Nikitin, E. B. *Angew. Chem., Int. Ed.* 2008, 47, 7924-7926.] Mascal and Nikitin use chloride stoichiometrically and produce potentially hazardous chlorinated organic products (chlorocarbons and chlorohydrocarbons) which are not observed in the methods of this invention. In addition, the weight of their reaction mixture is nearly 150-fold greater than that of the cellulose reactant. Their 1,2-dichloroethane extractant, which is likewise used in a large excess relative to cellulose, is a possible carcinogen, and the concentrated hydrochloric acid presents its own hazards. the methods herein can use the common industrial solvent, DMA, for example, that, along with LiCl enables the processing of cellulose at far higher concentrations (≤15 vs ≤7 wt %).

Example 8

Production of HMF from Carbohydrate Feedstocks

Carbohydrate feedstocks [including corn stover (34.4% cellulose), corn stover pre-treated with ammonia fiber explosion pretreatment (AFEX), and pine sawdust (40% cellulose)], LiCl, [EMIM]Cl, and DMA were mixed at 75° C. for 24 h. The carbohydrate feedstocks were used at 10 wt % loading. To this mixture were added concd HCl and catalyst in [EMIM]Cl, and the reaction mixture was stirred in a capped glass vial at the indicated temperature for the indicated time. At intervals aliquots of the reaction mixture were removed for HPLC analysis. The results are summarized in Table 6. Furfural was also formed from these carbohydrate feedstocks in up to 37% yield.

Efficient production of fuels or chemicals from crude biomass often requires pretreatment processes. [Chundawat, S. P. S.; Venkatesh, B.; Dale, B. E. *Biotechnol. Bioeng.* 2006, 96, 219-231; Aden, A. Biochemical Production of Ethanol from Corn Stover: 2007 State of Technology Model; Report NREL/TP-510-43205; National Renewable Energy Laboratory, Golden, Colo., 2008; http://www.nrel.gov/docs/fy08osti/43205.pdf.] In contrast, HMF can be produced readily from untreated lignocellulosic biomass such as corn stover or pine sawdust under conditions similar to those used for cellulose (Table 8). Yields of HMF from corn stover subjected to ammonia fiber expansion (AFEX) pretreatment were nearly identical to those for untreated stover. [Chundawat, S. P. S.; Venkatesh, B.; Dale, B. E. *Biotechnol. Bioeng.* 2006, 96, 219-231.]

TABLE 8

Production of HMF and Furfural from Carbohydrate Feedstocks[a]

| biomass | solvent | catalyst (mol %) | additives (wt %) | temp. (° C.) | time (h) | HMF[b]/Furfural[c] molar yield (%) |
|---|---|---|---|---|---|---|
| pine sawdust | DMA-LiCl (10%) | CrCl$_2$, 33 | [EMIM]Cl, 15 | 140 | 5 | 19 |
| pine sawdust | DMA-LiCl (10%) | CrCl$_3$, 33 | [EMIM]Cl, 15 | 140 | 5 | 17 |
| corn stover | DMA-LiCl (10%) | CrCl$_2$, 19 | [EMIM]Cl, 10 | 140 | 6 | 8 |
| corn stover | DMA-LiCl (10%) | CrCl$_2$, 38 | [EMIM]Cl, 10 | 140 | 6 | 16 |
| AFEX corn stover | DMA-LiCl (10%) | CrCl$_2$, 19 | [EMIM]Cl, 10 | 140 | 6 | 10 |
| AFEX corn stover | DMA-LiCl (10%) | CrCl$_2$, 38 | [EMIM]Cl, 10 | 140 | 6 | 16 |
| corn stover | DMA-LiCl (10%) | CrCl$_3$, 19 | [EMIM]Cl, 10 | 140 | 6 | 10 |

TABLE 8-continued

Production of HMF and Furfural from Carbohydrate Feedstocks[a]

| biomass | solvent | catalyst (mol %) | additives (wt %) | temp. (° C.) | time (h) | HMF[b]/Furfural[c] molar yield (%) |
|---|---|---|---|---|---|---|
| AFEX corn stover | DMA-LiCl (10%) | $CrCl_2$, 19 | [EMIM]Cl, 10 | 140 | 6 | 11 |
| corn stover | DMA-LiCl (10%) | $CrCl_2$, 10; HCl, 10 | [EMIM]Cl, 20 | 140 | 3 | 23 |
| corn stover | DMA-LiCl (10%) | $CrCl_2$, 10; HCl, 10 | [EMIM]Cl, 40 | 140 | 3 | 24 |
| corn stover | DMA-LiCl (10%) | $CrCl_2$, 10; HCl, 10 | [EMIM]Cl, 60 | 140 | 3 | 36 |
| corn stover | DMA-LiCl (10%) | $CrCl_2$, 10; HCl, 10 | [EMIM]Cl, 80 | 140 | 3 | 31 |
| corn stover | [EMIM]Cl | $CrCl_2$, 10; HCl, 10 | — | 140 | 3 | 29 |
| corn stover | DMA-LiCl (10%) | $CrCl_3$, 10; HCl, 10 | [EMIM]Cl, 20 | 140 | 3 | 26 |
| corn stover | DMA-LiCl (10%) | $CrCl_3$, 10; HCl, 10 | [EMIM]Cl, 40 | 140 | 1 | 39 |
| corn stover | DMA-LiCl (10%) | $CrCl_3$, 10; HCl, 10 | [EMIM]Cl, 60 | 140 | 1 | 40 |
| corn stover | DMA-LiCl (10%) | $CrCl_3$, 10; HCl, 10 | [EMIM]Cl, 60 | 140 | 2 | 48/34 |
| corn stover | DMA-LiCl (10%) | $CrCl_3$, 10; HCl, 10 | [EMIM]Cl, 80 | 140 | 2 | 47/37 |
| corn stover | [EMIM]Cl | $CrCl_3$, 10; HCl, 10 | — | 140 | 1 | 42 |

[a]Biomass was reacted at a concentration of 10 wt % relative to the total mass of the reaction mixture. The solvent composition is indicated by the wt % of LiCl relative to DMA with additive concentrations relative to the mass of the reaction mixture. Catalyst loading and yield are relative to moles of glucose monomers contained in the cellulose in the biomass. Yields are based on HPLC analysis.
[b]Yield from pine sawdust assumes a typical cellulose content of 40%; yields from corn stover are based on cellulose analysis of 34.4% for both AFEX-treated and untreated stover and xylan analysis of 22.8% for untreated stover.
[c]Molar yields from corn stover are based on xylan analysis of 22.8% for untreated stover.

Other biomass components, such as lignin and protein, did not interfere substantially in the process, as yields of HMF based on the cellulose content of the biomass were comparable to those from purified cellulose. To be highly efficient, a process for biomass conversion should also utilize the pentoses present in hemicellulose. Notably, the industrial chemical furfural is formed from the hemicellulose component of biomass under our reaction conditions in yields similar to those obtained in industrialprocesses (34-37% vs approximately 50%). [Zeitsch, K. J. *The Chemistry and Technology of Furfural and Its ManyBy-Products*; Elsevier: Amsterdam, 2000.]

Example 9

Synthesis of Furfural from Xylan

Exemplary results for conversion of xylan to furfural are provided in Tables 9A-9C at different reaction temperatrues as indicated. Xylan was reacted at a concentration of 5 wt % relative to the total mass of the reaction mixture. The solvent composition is indicated by the wt % of LiCl relative to DMA with additive concentrations relative to the mass of the reaction mixture. Catalyst loading and yield are relative to moles of xylose monomers contained in xylan. Yields are based on HPLC analysis. Xylan was reacted at a concentration of 5 wt % relative to the total mass of the reaction mixture. Birch xylan was used in all cases except where noted.

Representative Procedures:
A. Xylan (10.2 mg, 72 µmol) and concd HCl (1.6 µL, 19 µmol) were stirred in DMA (240 mg) at 140° C. for 2 h. Following addition of $CrCl_3$ (1 mg, 6 µmol), the reaction mixture was stirred at 120° C. for 2 h.
B. Xylan (6.0 mg, 43.5 µmol) and [EMIM]Cl (266.9 mg) were stirred at 85° C. for 24 h. Following addition of HCl (0.33 µL, 4 µmol) and $CrCl_2$ (0.8 mg, 6.5 µmol), the reaction mixture was stirred at 140° C. for 2 h.

TABLE 9A

Synthesis of Furfural from Xylan at 100° C.

| Solvent | Catalyst (mol %) | Additives (wt %) | time (h) | molar yield (%) |
|---|---|---|---|---|
| DMA-LiCl (10%) | HCl, 3 | | 4 | 0 |
| DMA-LiCl (10%) | HCl, 6 | | 4 | 1 |
| DMA-LiCl (10%) | HCl, 12 | | 4 | 0 |
| DMA-LiCl (10%) | $CrCl_2$, 6 | [EMIM]Cl, 5 | 4 | 0 |
| DMA-LiCl (10%) | $CrCl_2$, 6 | [EMIM]Cl, 10 | 4 | 0 |
| DMA-LiCl (10%) | $CrCl_2$, 6 | [EMIM]Cl, 20 | 4 | 0 |
| DMA-LiCl (10%) | $CrCl_3$, 6 | [EMIM]Cl, 5 | 4 | 0 |
| DMA-LiCl (10%) | $CrCl_3$, 6 | [EMIM]Cl, 10 | 4 | 1 |
| DMA-LiCl (10%) | $CrCl_3$, 6 | [EMIM]Cl, 20 | 4 | 0 |
| DMA-LiCl (10%) | HCl, 3 | [EMIM]Cl, 10 | 4 | 0 |
| DMA-LiCl (10%) | HCl, 6 | [EMIM]Cl, 10 | 4 | 0 |
| DMA-LiCl (10%) | HCl, 12 | [EMIM]Cl, 10 | 4 | 1 |

Conversion of xylan into furfural was significantly more difficult than dehydration of xylose. Birchwood xylan, the typical material used in these studies, was not readily soluble in DMA. Instead, it was solubilized by heating and stirring in DMA with LiCl or LiBr at 80-120° C. for several hours. Xylan dissolved in DMA-LiCl precipitated by addition of water, indicating that it was not fully depolymerized into xylose under these conditions. Initially, conversion of xylan at 100° C. using conditions similar to those used successfully with xylose (Example 6). With xylan, however, only trace yields of fufural were obtained. Slightly higher yields were possible from reactions performed at 120° C. (Table 9B), suggesting that a reaction temperature of 100° C. conditions was too low to depolymerization of xylan into xylose.

TABLE 9B

Synthesis of Furfural from Xylan at 120° C.

| solvent | catalyst (mol %) | additives (wt %) | time (h) | molar yield (%) |
|---|---|---|---|---|
| DMA-LiCl (10%) | CrCl$_2$, 6 | | 4 | 0 |
| DMA-LiCl (10%) | CrCl$_3$, 6 | | 4 | 4 |
| DMA-LiCl (10%) | CrCl$_2$, 6 | [EMIM]Cl, 10 | 4 | 0 |
| DMA-LiCl (10%) | CrCl$_2$, 6 | [EMIM]Cl, 20 | 4 | 3 |
| DMA-LiCl (10%) | CrCl$_3$, 6 | [EMIM]Cl, 10 | 4 | 3 |
| DMA-LiCl (10%) | CrCl$_3$, 6 | [EMIM]Cl, 20 | 4 | 0 |

TABLE 9C

Synthesis of Furfural from Xylan at 140° C.

| biomass | solvent | catalyst (mol %) | additives (wt %) | time (h) | molar yield (%) |
|---|---|---|---|---|---|
| xylan | DMA-LiCl (10%) | CrCl$_2$, 6 | [EMIM]Cl, 5 | 2 | 8 |
| xylan | DMA-LiCl (10%) | CrCl$_2$, 6 | [EMIM]Cl, 10 | 2 | 7 |
| xylan | DMA-LiCl (10%) | CrCl$_3$, 6 | [EMIM]Cl, 20 | 2 | 1 |
| xylan | [EMIM]Cl | CrCl$_2$, 10; HCl, 10 | | 2 | 18 |
| xylan (oat) | [EMIM]Cl | CrCl$_2$, 10; HCl, 10 | | 2 | 25 |
| xylan (beech) | [EMIM]Cl | CrCl$_2$, 10; HCl, 10 | | 2 | 11 |
| corn stover[a] | [EMIM]Cl | CrCl$_2$, 10; HCl, 10 | | 2 | 22 |

[a]Yield from corn stover is based on xylan content of 22.8%. Yields are based on HPLC analysis.

By increasing the reaction temperature to 140° C., 7-8% yields of furfural were obtained using CrCl$_2$, although CrCl$_3$ was less effective (Table 9C). Adding HCl to the reaction mixture as a co-catalyst for xylan saccharification and using [EMIM]Cl as the solvent improved the yield of furfural to 18%. Disparate yields under these conditions were obtained with xylan form different sources suggesting significant differences in xylan recalcitrance among biomass sources. These results imply that the depolymerization is a barrier for chromium-catalyzed furfural production from xylan.

To increase yield, xylan was treated with HCl at 140° C. prior to addition of the chromium catalyst to increase saccharification of xylan prior to furfural synthesis. HCl-treated xylan was then reacted at 120° C. (Table 9D). This process enabled furfural yields similar to those obtained at 140° C. Use of HCl during the solubilization step was needed for furfural production, while HCl alone did not result in yields as high as those obtained with both chromium and HCl. The effects of other additives such as LiCl, LiBr, and ionic liquids were modest. These data suggest that pre-treatment of xylan to form xylose improves furfural yields. Using HCl in aqueous-ionic liquid mixtures, we have demonstrated that birchwood xylan can be hydrolyzed to xylose in up to 77% yield. A combination of this hydrolysis process with chromium catalysts for mild conversion of xylose into furfural may allow efficient transformation of xylan into furfural.

TABLE 9D

Synthesis of Furfural from Xylan after HCl Treatment[a]

| solvent | catalyst (mol %) | additives (wt %) | time (h) | molar yield (%) |
|---|---|---|---|---|
| DMA | HCl, 25 | | 2 | 7 |
| DMA | CrCl$_3$, 6 | | 2 | 0 |
| DMA | CrCl$_3$, 6; HCl, 25 | | 2 | 11 |
| DMA | HCl, 25 | [EMIM]Cl, 5 | 2 | 10 |
| DMA | CrCl$_3$, 6 | [EMIM]Cl, 10 | 2 | 3 |
| DMA | CrCl$_3$, 6; HCl, 25 | [EMIM]Cl, 20 | 2 | 15 |
| DMA-LiCl (10%) | CrCl$_2$, 6; HCl, 25 | | 2 | 7 |
| DMA-LiCl (10%) | CrCl$_3$, 6; HCl, 25 | | 2 | 4 |
| DMA-LiCl (10%) | CrCl$_2$, 6; HCl, 25 | | 2 | 6 |
| DMA-LiCl (10%) | CrCl$_3$, 6; HCl, 25 | | 2 | 6 |
| DMA-LiCl (5%) | CrCl$_2$, 6; HCl, 25 | | 2 | 6 |
| DMA-LiCl (5%) | CrCl$_3$, 6; HCl, 25 | | 2 | 6 |
| DMA-LiCl (5%) | CrCl$_2$, 6; HCl, 25 | [EMIM]Cl, 5 | 2 | 8 |
| DMA-LiCl (5%) | CrCl$_2$, 6; HCl, 25 | [EMIM]Cl, 10 | 2 | 4 |
| DMA-LiCl (5%) | CrCl$_3$, 6; HCl, 25 | [EMIM]Cl, 5 | 2 | 0 |
| DMA-LiCl (5%) | CrCl$_3$, 6; HCl, 25 | [EMIM]Cl, 10 | 2 | 8 |
| DMA | CrCl$_2$, 6; HCl, 25 | [BMIM]Br, 20 | 2 | 6 |
| DMA | CrCl$_2$, 6; HCl, 25 | LiBr, 10 | 2 | 11 |

[a]Xylan was reacted at a concentration of 5 wt % relative to the total mass of the reaction mixture. The solvent composition is indicated by the wt % of LiCl relative to DMA with additive concentrations relative to the mass of the reaction mixture. Catalyst loading and yield are relative to moles of xylose monomers contained in xylan. Yields are based on HPLC analysis.

Example 10

Production of DMF from Fructose

Fructose (1.805 g, 10 mmol) and LiCl (1.690 g) were dissolved in DMA (14.67 g). Following addition of concd H$_2$SO$_4$ (33 µL, 0.6 mmol), the reaction mixture was stirred at 120° C. for 1 h. A portion of the reaction mixture (3.01 g, 16.5%) was then diluted with deionized water (2 g), loaded on an ion-exclusion column (Dowex 50X8-200, Li$^+$ form, 70 cm×1.5 cm), and eluted with deionized water. HMF-containing fractions with conductivity less than 50 µS were pooled and concentrated under high vacuum. The residue was taken up in 1-butanol (45 g) and placed in a Parr reactor with Cu:Ru/carbon catalyst (100 mg). The reactor was purged three times with H$_2$(g), pressurized with 6.8 bar H$_2$(g), and heated to 220° C. with stirring. After 10 h, the reactor was cooled and vented. The contents were analyzed by HPLC for DMF (51.6 mg, 537 µmol, 32.5% molar yield based on fructose).

Example 11

Production of DMF from Corn Stover

Corn stover (1.504 g, 3.19 mmol glucose units in cellulose), LiCl (0.755 g), [EMIM]Cl (5.630 g), and DMA (6.756 g) were mixed at 75° C. for 24 h. To this viscous mixture were added conc'd HCl (26 µL, 310 µmol) and CrCl$_3$ (50.5 mg, 319 µmol) in [EMIM]Cl (0.55 g), and the reaction mixture was heated with 140° C. with vigorous stirring. After 2 h, the reaction mixture was cooled to room temperature, diluted with deionized water (7 g), and centrifuged to sediment insoluble material. After removal of the supernatant, the pellet was resuspended in deionized water (3 g), and the process repeated. The combined supernatant solutions were loaded on an ion-exclusion column (Dowex 50X8-200, Li$^+$ form, 70 cm×1.5 cm), and eluted with deionized water. HMF-containing fractions with conductivity less than 50 µS were pooled and concentrated under high vacuum. Following concentration under high vacuum, the pooled HMF-containing fractions with conductivity more than 50 µS were loaded a second time on the ion-exchange column and eluted with deionized water. HMF-containing fractions from the second pass with conductivity less than 50 μS were pooled, concentrated under high vacuum, and combined with the earlier HMF concentrate. This residue was taken up in 1-butanol (45 g) and placed in a Parr reactor with Cu:Ru/carbon catalyst (79 mg). The reactor was purged three times with $H_2$ (g), pressurized with 6.8 bar $H_2$(g), and heated to 220° C. with stirring. After 10 h, the reactor was cooled and vented. The contents were analyzed by HPLC for DMF (27.7 mg, 288 μmol, 9.0% molar yield based on cellulose content of corn stover).

Figure 4:
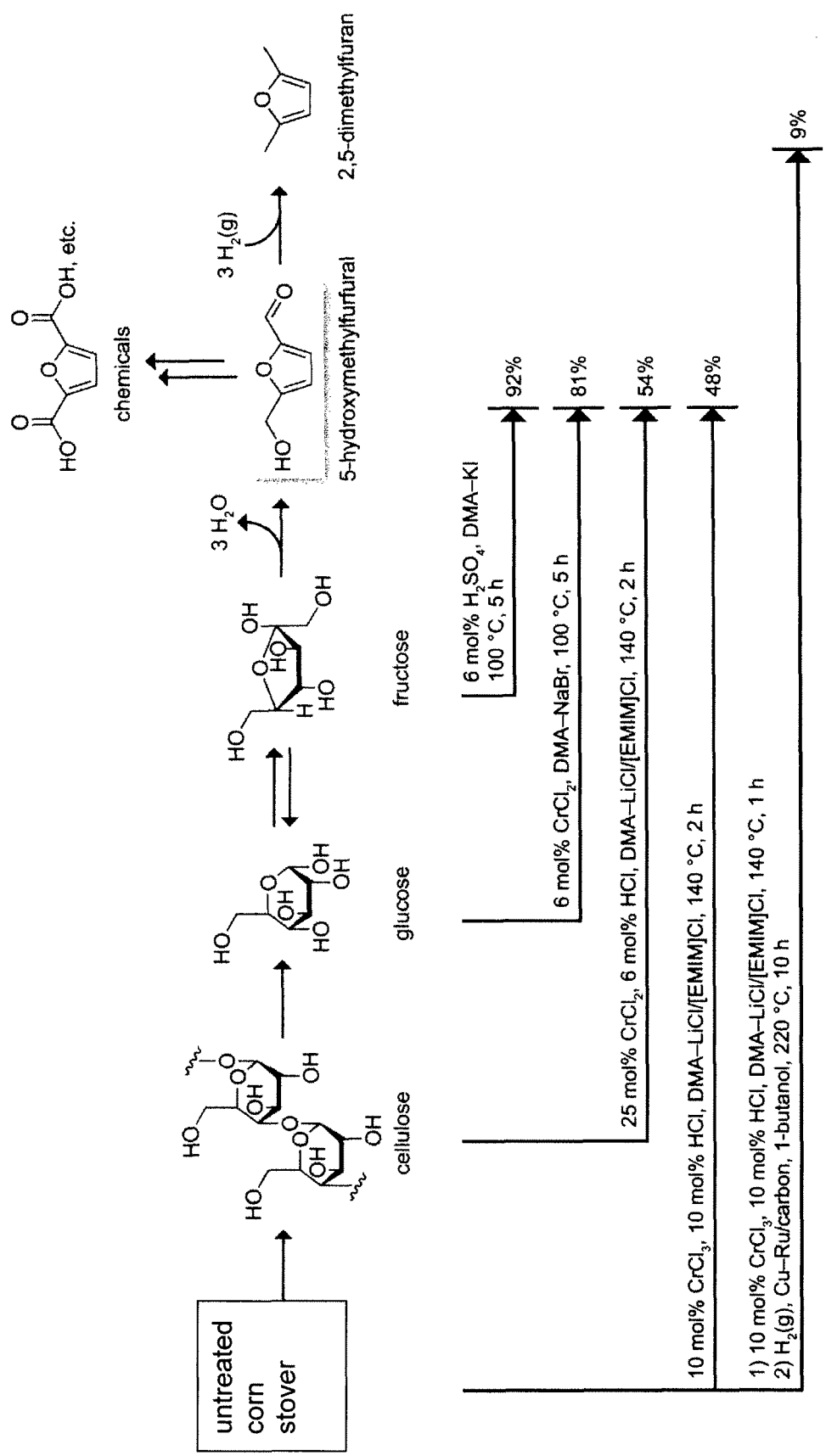
FIG. 4 provides a summary of exemplary reaction of the present invention, illustrating exemplary reaction conditions and exemplary reaction yields.

The conversion of lignocellulosic biomass to HMF in a single step offers straightforward access to a wide variety of useful HMF derivatives, such as DMF. Dumesic and co-workers have shown that DMF, a promising HMF-derived fuel, can be prepared by hydrogenolysis of fully purified HMF using copper catalysts. [Nisbet, H. B. *J. Inst. Petrol.* 1946, 32, 162-166; Roman-Leshkov, Y.; Barrett, C. J.; Liu, Z. Y.; Dumesic, J. A. *Nature* 2007, 447, 982-986.] Using the process of this invention, DMF is synthesized in two chemical reactions from lignocellulosic biomass. In the first step HMF is formed from untreated corn stover in DMA-LiCl. The chloride ions are then removed from the crude HMF by ion-exclusion chromatography in water. [Rapp, K. M. U.S. Pat. No. 4740605, 1988; Fritz, J. S. *J. Chromatogr.* 1991, 546, 111-118.] This separation step prevented the chloride from poisoning the copper hydrogenolysis catalyst. The crude HMF from corn stover is then subjected to hydrogenolysis in 1-butanol with a carbon-supported copper-ruthenium catalyst to obtain a 49% molar yield of DMF, similar to that obtained by Dumesic and co-workers using HMF that contained trace chloride. The unoptimized overall molar yield of DMF based on the cellulose content of the stover was 9% (FIG. 4).

We claim:

1. A method for converting a carbohydrate to a furan which comprises the steps of:
    (a) preparing a mixture of the carbohydrate in a polar aprotic solvent containing a chromium halide; and
    (b) heating the mixture to obtain a furan,
wherein the carbohydrate is a lignocellulosic feedstock and the polar aprotic solvent is an ionic liquid.

2. The method of claim 1 wherein the furan is 5-hydroxymethylfurfural or furfural.

3. The method of claim 1 wherein the ionic liquid is selected from an alkylimidazolium ionic liquid, an alkylimidazolium halide ionic liquid, an alkylimidazolium chloride ionic liquid, an alkylpyridinium ionic liquid, an alkylpyridinium halide ionic liquid, an alkylpyridinium chloride ionic liquid or a combination thereof.

4. The method of claim 3 wherein the ionic liquid is selected from [EMIM]Cl, [BMIM]Cl, [EMIM]Br, 1-ethyl-2, 3-dimethylimidazolium chloride, 1-ethylpyridinium chloride, 1-butyl-4-methylpyridinium chloride, or a mixture thereof.

5. A method for making 2, 5-dimethylfuran which comprises the step of making 5-hydroxymethylfurfural by the method of claim 1 and thereafter converting 5-hydroxymethylfurfural to 2, 5-dimethylfuran.

6. A method for making furan which comprises the step of making furfural by the method of claim 1 and thereafter converting furfural to furan.

7. The method of claim 1 wherein the mixture further comprises acid.

8. The method of claim 7 wherein the acid is HCl.

9. The method of claim 1 wherein the chromium halide is a chromium chloride.

10. The method of claim 1 wherein the chromium halide is $CrBr_3$.

11. The method of claim 1 wherein the lignocellulosic feedstock is corn stover.

12. The method of claim 1 wherein the mixture is heated to 80 to 140° C.

13. The method for making 2, 5-dimethylfuran of claim 5 wherein 5-hydroxymethylfurfural is converted to 2, 5-dimethylfuran by hydrogenolysis.

14. The method for making furan of claim 6 wherein furfural is converted to furan by decarbonylation.

* * * * *